United States Patent [19]

Timmons et al.

[11] Patent Number: 5,276,240

[45] Date of Patent: Jan. 4, 1994

[54] CATALYTIC HYDRODEHALOGENATION OF POLYHALOGENATED HYDROCARBONS

[75] Inventors: Richard B. Timmons; Wen-Long Jang; Yigong He, all of Arlington; David J. Houpt, Jr., Benbrook, all of Tex.

[73] Assignee: Board of Regents, The University of Texas System, Austin, Tex.

[21] Appl. No.: 962,997

[22] Filed: Oct. 16, 1992

Related U.S. Application Data

[63] Continuation of Ser. No. 778,735, Oct. 18, 1991, abandoned.

[51] Int. Cl.$^5$ .............................................. C07C 1/26
[52] U.S. Cl. ..................................... 585/642; 585/638; 585/641; 585/733; 570/227
[58] Field of Search ............... 585/408, 485, 638, 639, 585/640, 641, 642, 733; 570/227; 588/206, 207, 248

[56] References Cited

U.S. PATENT DOCUMENTS

| | | | |
|---|---|---|---|
| 3,894,107 | 7/1975 | Butter et al. | 585/408 |
| 4,046,825 | 9/1977 | Owen et al. | |
| 4,049,738 | 9/1977 | Young | 585/454 |
| 4,112,056 | 9/1978 | Chen et al. | 423/329 |
| 4,144,192 | 3/1979 | Reinhardt, III | 252/438 |
| 4,306,106 | 12/1981 | Kerr et al. | 585/640 |
| 4,384,159 | 5/1983 | Diesen | 585/642 |
| 4,652,688 | 3/1987 | Brophy et al. | 585/408 |

FOREIGN PATENT DOCUMENTS

2438252 8/1974 Fed. Rep. of Germany.

OTHER PUBLICATIONS

Weiss et al; "Hydrodechlorination and Oligomerization of Carbon Tetrachloride over Nickel Y Zeolites": *Journal of Catalysis*, 1982, 74, 136-143.

Chemical Abstracts vol. 91: No. 63337Q.

Oku, et al., "Complete Destruction of Tetra- and Tri-Chloroethylene by Reductive Dechlorination Using Sodium Naphthalenide", *Chemistry Express*, 5, 181-184 (1990).

Chuang, et al., "Gas-Phase Reactions of Chloroform and 1,1,2-Trichloroethane with Hydrogen in a Tubular Flow Reactor," *Ind. Eng. Chem. Process. Des. Dev.*, 25, 317-321 (1986).

Gokhberg, et al., "Heterogeneous Catalytic Dehydrochlorination of 1,1,2-Trichloroethane. III. Study of the Features of Deactivation of Silica Gel Modified with Alkali Metal Compounds," *Kinetika i Kataliz*, 30, 1376-1380 (1989).

Bartholomew, et al., "Chemistry of Nickel-Alumina Catalysts," *J. Catalysis*, 45, 41-53 (1976).

Mochida, et al., "Linear Free-Energy Relationships in Heterogeneous Catalysis. VI. Catalytic Elimination Reaction of Hydrogen Chloride from Chloroethanes on Solid Acids and Bases," *J. Org. Chem.*, 32, 3894-3898 (1967).

Mochida, et al., "Dehydrochlorination and Dechlorina- (List continued on next page.)

Primary Examiner—Asok Pal
Assistant Examiner—P. Achutamurthy
Attorney, Agent, or Firm—Arnold, White & Durkee

[57] ABSTRACT

A novel catalytic process involving complete hydrodehalogenation of halogenated aliphatic hydrocarbons in the presence of a hydrogen donor and a modified zeolite catalyst has been developed. The process is operated in a continuous flow mode and reaction products consist exclusively of hydrogen halide and hydrocarbons. The relative ratio of paraffins to olefins to aromatics obtained in the product distribution is a strong function of the ratio of hydrogen to reactant and the space velocity and temperature employed. The catalyst employed is a nickel metal modified shape selective zeolite that takes advantage of the hydrogenolysis ability of nickel and the acidic-shape selective properties of the zeolite.

17 Claims, 3 Drawing Sheets

OTHER PUBLICATIONS tion of Chloroethanes on Chromia Catalyst," *J. Org. Chem.* 5, 33, 2163–2165 (1968).

Mochida et al., "Elimination Reaction of Hydrogen Chloride from 1,1,2-Trichloroethane on Ion-Exchanged Molecular Sieves," *J. Org. Chem.*, 33, 2161–2163 (1968).

Mochida et al., "Catalytic Dehydrochlorination over Alumina Promoted by Steam," *J. of Catalysis*, 51, 72–79 (1978).

Mochida et al., "Selective Dehydrochlorination of Ethylene Chlorohydrin over Acid-Proof Basic Catalysts Recovering Dry Hydrogen Chloride," *Ind. Eng. Chem. Prod. Res. Dev.*, 22, 38–40 (1983).

Mochida et al., "Catalytic Dehydrochlorination of 3,4-Dichloro-1-butene over CsCl Supported on Silica Gel," *Ind. Eng. Chem. Prod. Res. Dev.*, 25, 496–499 (1986).

Imamura et al., "Decomposition of 1,2-Dichloroethane on $TiO_2/SiO_2$," *Ind. Eng. Chem. Res.*, 28, 1449–1452 (1989).

Helt, J. E., "Biofuels and Municipal Waste Technology Research Program Summary: FY 1986," DOE Report NTIS, PC A16/MF AO1, *Energy Research Reports*, 1987.

Shishkov, et al., "Catalytic Conversion of Thiophene and Mercaptans on a Cobalt-Molybdenum Catalyst," *Dokl. Bolg. Akad. Nauk.*, 35, 45–48 (1982).

Naum, et al., "Statistical-Mathematical Analysis of the Influence of Y Zeolite Catalysts in Various Polycationic Forms on the Conversion of Hydrodechlorination Reaction of Some Chlorinated Organic Compounds. I. Hydrodechlorination of Chlorobezene," *Bul. Inst. Politech, Iasi*, sec. 2, *Chim Ing. Chim.*, 25, number 1–2, 53–58 (1979).

Dialog Search Report.

CATALYTIC HYDRODEHALOGENATION OF POLYHALOGENATED HYDROCARBONS

This is a continuation of co-pending application Ser. No. 07/778,735, filed on Oct. 18, 1991, now abandoned.

BACKGROUND OF THE INVENTION

1. Field of the Invention

The invention relates to a catalytic process for complete removal of heteroatoms from heteroatom-containing aliphatic hydrocarbons using a nickel-containing zeolite catalyst and is particularly suited for hydrodehalogenation of polyhalogenated compounds. The process is characterized by high conversion efficiencies without rapid catalyst deactivation. Ratios of paraffinic and aromatic products may be altered by modification of reaction conditions.

2. Description of Related Art

Various heteroaliphatic compounds are widely used commercially and industrially as solvents or reactants in the production of plastics, herbicides and other products. Unfortunately, many of these compounds are toxic and have posed significant problems in disposing of waste and residual material.

Present methods of disposing of toxic materials, particularly low molecular weight chlorinated liquid compounds, are not satisfactory. Landfills are inadequately protected against runoff or leakage into underground water supplies. Incineration frequently does not provide complete breakdown and in fact may produce other toxic compounds which are discharged into the atmosphere. Moreover, complete combustion of some compounds often requires high temperatures to obtain desired efficiency, resulting in high expenditure of energy.

Among the most common waste products are haloorganic compounds, including chlorinated hydrocarbons. There have been efforts to Develop efficient processes for removing one or more chlorine atoms from these compounds, especially the volatile chlorinated organics. A proposed alternative to incineration is biological and chemical waste conversion. In one example, chemical destruction of tetra- and trichloroethylenes in solution was achieved by reductive dechlorination with sodium naphthalenide (oku and Kimura, 1990). Another example of chemical destruction is the high-temperature gas phase reductive dehydrochlorination of chloroform and 1,1,trichloroethane by direct reaction with molecular hydrogen (Chuang and Bozzelli, 1986).

The major difficulty encountered in chemical reductive dehydrochlorination of these solvents is that many industrially important polychlorinated compounds, such as carbon tetrachloride, trichloroethanes, trichloroethylene, etc., are difficult to completely dechlorinate using economically acceptable routes. In principle, a catalytic process offers possibilities for chemical conversions and a number of studies have focused on hydrodehalogenation. However, these studies have been limited to only partial removal of the halogen, as in dehydrochlorination of 1,1,2-trichloroethane to 1,1-dichloroethylene over alumina (Mochida et al., 1978) or to mixtures of 1,1- and 1,2-dichloroethylenes over an alkali ion/$SiO_2$ catalyst (Gokhberg et al., 1989). Also, zeolite catalysts have been employed to achieve partial dechlorination of a variety of di- and tri-chlorinated hydrocarbons (Diesen, 1983). Attempts at more extensive catalytic dechlorinations with zeolite Y and mordenite catalysts have resulted in rapid catalyst inactivation due to deposition of carbonaceous material on the catalyst surface (Imamura et al., 1989; Weiss et al., 1982). As illustrated in the present application, shape selective zeolite catalysts, similar in composition to those employed by Diesen (1983) and Butter, et al. (1975) also exhibit rapid catalyst deactivation when employed under reaction conditions in which complete dechlorination of polychlorinated reactants is attempted.

In general, efforts to remove multiple chlorine atoms from hydrocarbon compounds have not been successful, particularly where zeolite catalysts have been used. To date, every reported catalyst study in which complete dehalogenation of polyhalogenated reactants was attempted has failed as a result of rapid catalyst deactivation. Major drawbacks of attempts to use catalytic methods include inefficiency of the dechlorination process, relatively rapid poisoning or inactivation of the catalyst and/or economically unacceptable routes of conversion.

SUMMARY OF THE INVENTION

The present invention provides the first successful continual catalytic process for the complete hydrodehalogenation of polyhalogenated molecules. The method is especially efficient in dehydrohalogenation of polychlorinated aliphatic hydrocarbons. The process of the invention generally results in 100% conversion to hydrocarbons and hydrogen chloride, without rapid deactivation of the metal-containing zeolite catalyst used in the conversion reaction.

The process developed is also successful in the removal of heteroatoms from a wide range of heteroatom-containing organic compounds. Examples of heteroatom-containing feedstock compounds include oxygen, sulfur, nitrogen and halogen-containing aliphatic hydrocarbon compounds.

In the practice of the present invention, one generally utilizes a continuous flow process wherein a gaseous phase containing one or more heteroatom-containing aliphatic hydrocarbons is passed over a nickel metal-containing zeolite catalyst. The feedstream typically includes a hydrogen donor. The reaction is generally conducted at temperatures above 300° C.

In one aspect of the invention, feedstocks containing one or more halogenated hydrocarbons are completely converted to nonhalogen containing hydrocarbons in the gaseous phase using initial conversion temperatures between about 300° and 500° C., preferably 450° C., for a period of time sufficient to initiate conversion to nonhalogen containing products. Although the time of contact at the initiation temperature may vary depending on the halogenated hydrocarbon and the hydrogen donor used in the feedstock, the inventors have found that about one hour at the initiation temperature is satisfactory. Once initiated, the reaction temperature may be lowered to approximately 325° C. At this temperature 100% conversion will continue at the same efficiencies in product distributions as observed at constant temperatures of 350° C. and above.

The catalyst found useful for this reaction is a metal-modified zeolite catalyst. A ZSM-5 zeolite catalyst containing free nickel metal is particularly preferred. Efficient halogen stripping from polyhalogenated aliphatic hydrocarbons is not observed unless the catalyst contains elemental nickel metal. ZSM-5 zeolite catalyst alone, aluminum oxide or ZSM-5/$Al_2O_3$ catalyst do not provide efficient conversions of polychlorinated materials such as, for example, 1,1,1-trichloroethane. Pure HZSM-5 catalyst, for example, is rapidly deactivated when hydrodechlorination of 1,1,1-TCA is attempted. This loss of activity may be attributed to coke formation on the catalyst as revealed by spectroscopic and scanning electron microscopy (SEM) analysis. SEM analysis of spent catalysts reveals tiny fibers of coke on the exterior surface sites.

In contrast to pure ZSM-5 or $Al_2O_3$ catalysts, the nickel ZSM-5/$Al_2O_3$ bifunctional catalysts used in the method of this invention when combined with addition of an appropriate hydrogen donor to a feedstock stream containing a polyhalogenated aliphatic hydrocarbon achieves dechlorination of these molecules without experiencing rapid catalysts inactivation. An effective catalyst is prepared by mixing ZSM-5/$Al_2O_3$ with an aqueous solution of a nickel salt such as nickel nitrate. The $Ni(NO_3)_2$/ZSM-5/$Al_2O_3$ mixture obtained after drying is calcined to convert the nickel nitrate to nickel oxide which is subsequently reduced to elemental nickel such as by hydrogen reduction. As shown by scanning electron microscope analysis, micron sized groupings of nickel atoms are disbursed uniformly throughout the solid sample. Percent nickel loading may be controlled by variation of the concentration of the nickel salt used in the original aqueous solution. Typically, nickel loadings from 10%-35% provide an efficient catalyst, although hydrodehalogenations have been observed with nickel loadings as low as 1%. At low percent loadings, however, catalyst efficiency rapidly deteriorates, usually within the first few hours of the conversion reaction.

While the invention has been illustrated with a ZSM-5 zeolite, it is anticipated that the catalyst is not necessarily limited to the ZSM-5 type zeolite. Other synthetic shape selected zeolites with other pore sizes and activity expected to be useful are available for example, ZSM-11 and ZSM-22 and the like. Moreover, although the catalyst used in demonstrating this invention has a silicon to aluminum ratio of 30 to 1, it is in fact possible to vary this silicon to aluminum ratio from approximately 10 to 120 while maintaining the ZSM-5 pore structure. It is well known that the relative strength of the catalytic acid sites increases with decreasing aluminum content in ZSM-5 materials. Therefore, it is expected that catalyst formulation with respect to catalyst activity and longevity may be improved by changing the silicon aluminum ratios in selected zeolite catalysts.

Feedstocks used in the conversion reaction typically comprise an aliphatic polyhalogenated hydrocarbon and a hydrogen donor. A hydrogen donor is used in order to obtain and maintain complete dechlorination of the polychlorinated reactants. Generally, it has been found that hydrogen, or hydrogen in combination with water or methanol, may serve as hydrogen donors. When hydrogen alone is used as a hydrogen donor, an excess of hydrogen over the organic reactant is generally employed. The excess hydrogen may be recycled in the reaction. Increased economy of the conversion may be obtained by combining hydrogen with other hydrogen donor additives such as water or methanol. Water and methanol are particularly attractive because they are less expensive than hydrogen and may be used with hydrogen for efficient conversion to products.

Continuous dechlorination has been found to occur with temperatures on the order of about 325° C. and higher. At lower temperatures catalyst lifetimes have decreased, apparently due to coke deposition. With respect to commercialization, the lower the reaction temperature the more attractive the process economics with respect to energy consumption, capital equipment costs, and maintenance needs. It will be appreciated that lower operating temperatures may be achieved via improvements in both catalyst composition and/or the nature and concentration of the hydrogen donor atoms added to the reaction feed. While variation is possible, the inventors have found that, in general, the reaction may typically be run efficiently between about 300° and 500° most preferably at a temperature between about 350° and 400° C. Alternatively, the reaction may be initiated at a temperature of 350° or above and subsequently lowered to a maintenance temperature of around 325° C. It has been found that if the reaction is not initiated at the higher temperature before dropping the temperature to about 325° C., reaction efficiency decreases.

While the invention has been demonstrated with a nickel metal loaded zeolite catalyst, it should be noted that many other transition metals besides nickel also exhibit hydrogenolysis activity; for example, metals such as cobalt, ruthenium, rhodium, platinum and palladium are used extensively for this purpose. Expense might be one factor to consider in developing other metal loaded zeolite catalyst for the practice of the present invention. Cobalt and iron may be attractive for consideration because they are relatively inexpensive. Moreover, it may well be that selective use of small amounts of rare metals in combination with larger amounts of elements such as nickel, cobalt and the like may be especially useful without adding unduly to the expense. Alternatively, mixed metal containing zeolite catalysts, as well as the presence of various metal ions either entrapped or as part of the framework are not intended to be excluded from the ambit of the invention.

An important aspect of the invention is the ability of the catalyst to convert polyhalogenated compounds completely to products free of the halogen atoms. Examples of compounds that may be totally converted to the corresponding hydrogen halide and hydrocarbon reaction products are trichloroethylenes and trichloroethanes. Typical examples of polychlorinated hydrocarbons include 1,1-dichloroethane, 1,1-dichloroethylene, 1,2-dichloromethane, 1,1,1- and 1,1,2-trichloromethane and the like. Perchlorinated hydrocarbons such as tetrachloroethylene are also readily hydrodechlorinated using the process of the invention.

Additionally, the inventors' hydrodehalogenation process readily hydrodebrominates polybrominated aliphatic hydrocarbons, including 1,2-dibromoethane and like compounds. The conversion process may also be practiced with a wide range of other materials containing hetero atoms such as oxygen, nitrogen or sulfur, represented by common solvent and liquid wastes such as ethyleneglycol, acetone, various alcohols and a variety of sulfur-containing compounds. One hundred percent conversion of these compounds to pure hydrocarbons has been demonstrated using the described process.

Mixed halogenated compounds are also hydrodehalogenated. A particular compound of interest is trichlorotrifluoroethane, shown to be completely dehalogenated using the disclosed process. Several modifications of the reaction conditions are envisioned, particularly in devising methods to alleviate potential adverse effects of hydrogen fluoride that may affect the integrity of the catalyst. Methods such as adsorption or reaction with added neutralizing substances in the feedstream would be a consideration.

It will be appreciated that it may be desirable to alter the ratio of distribution products obtained from the various reactants that might be employed. This is readily achieved by altering hydrogen to reactant ratio, temperature and/or space velocity. Such changes, improvements and modifications are well within the range of practice and knowledge to those of skill in the art.

DETAILED DESCRIPTION OF THE INVENTION

Reactor

Figure 1:
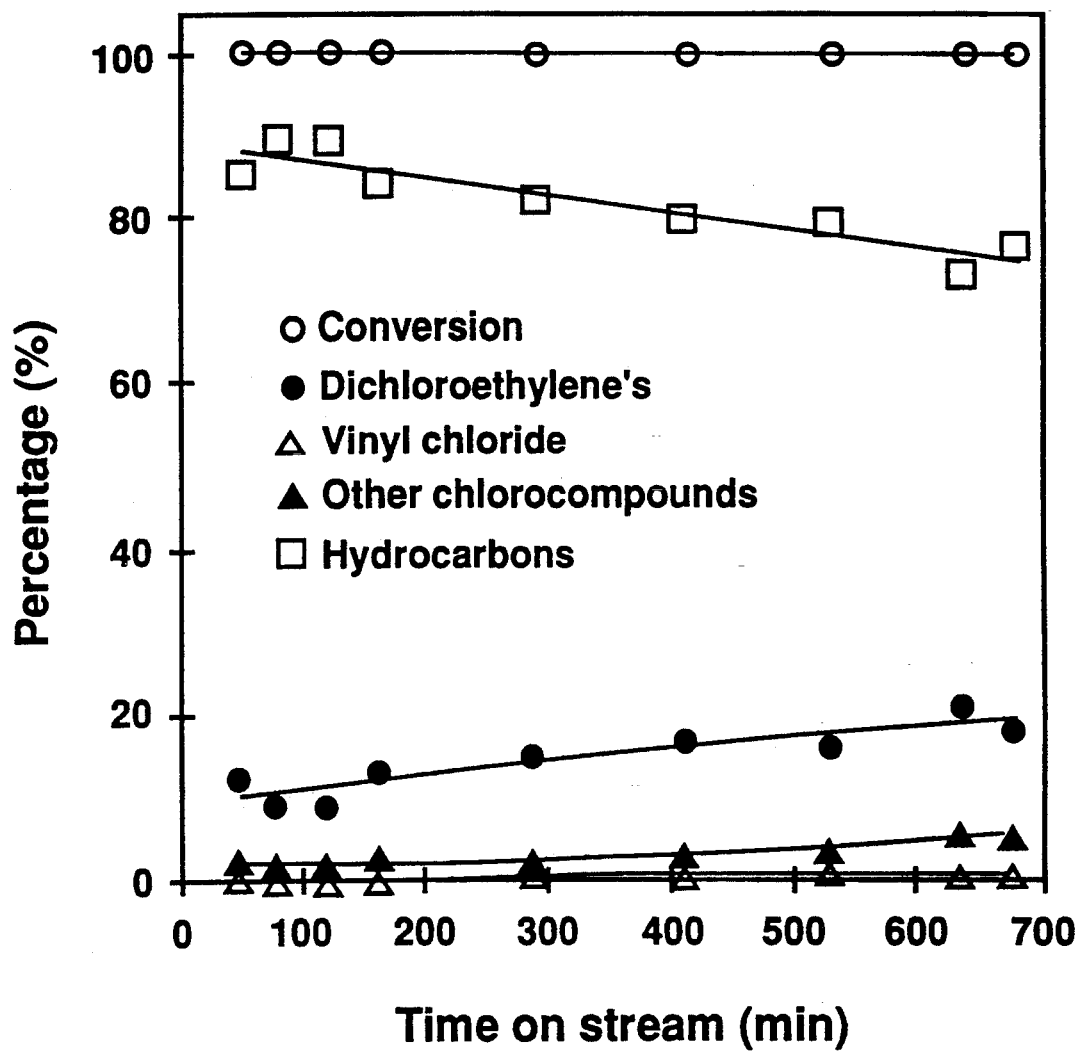
FIG. 1 shows the product distribution in conversion of trichloroethylene over 10% Ni/H-ZSM-5/Al$_2$O$_3$ in the presence of hydrogen and water at a constant temperature of 425° C.

A fixed-bed continuous flow microreactor operating at atmospheric pressure was employed. Catalyst was placed in the center of a ¼ inch×6 inch stainless steel reactor tube mounted vertically in a bored cylindrical block aluminum furnace. The furnace temperature was adjusted and maintained using an Omega Engineering CN-2010 Series programmable temperature controller. Gas flows (H$_2$ and He) were measured using calibrated flow meters. The liquid reactant was provided to the reactor by bubbling hydrogen through a thermostated container of the liquid. All transfer lines were heated to eliminate condensation of the liquid. The amount of liquid reactant provided as vapor was determined by periodic weighing of the liquid containing vessel. Conversion studies were carried out over a temperature range of 250° to 450° C. using 400 mg samples of catalyst.

Catalyst

The particular form of ZSM-5 used in the present work had a silicon to aluminum ratio of 30. The sodium cations present in the zeolite were exchanged for NH$_4$+ by contacting the catalyst with a solution of (NH$_4$)$_2$SO$_4$. Specifically, this cation exchange was carried out using weight ratios of 1 g (NH$_4$)$_2$SO$_4$: 1 g ZSM-5: 10 g H$_2$O. The NH$_4$-ZSM-5 material so obtained was dried at 120° C. and then calcined at 550° C. for 3 hours. The resulting solid was mixed with 0.5 M HNO$_3$ at 70° C. for 4 hours at a mixing ratio of 1 g of catalyst per 40 mL of HNO$_3$ solution. The solid catalyst in the form of H-ZSM-5 was filtered from solution and dried at 120° C. The resulting solid was blended with Al(OH)$_3$ at a weight ratio of 40 parts zeolite to 60 parts Al(OH)$_3$. This blend was then added to a solution of nickel(II) nitrate and the resulting solution evaporated to dryness. The nickel loading of the final catalyst was determined by the volume and concentration of the Ni(NO$_3$)$_2$ solution employed. The resulting solid obtained was then calcined at 550° C. for 2 hours to convert the Ni(NO$_3$)$_2$ to nickel oxide and the Al(OH)$_3$ to Al$_2$O$_3$. The resultant solid NiO/ZSM-5/Al$_2$O$_3$ was cracked and sieved to 18-50 mesh (i.e., 1000 to 300 micron sized particles). The nickel oxide was reduced to elemental nickel immediately prior to use by hydrogen reduction. Alternately the high temperature calcination of Ni(NO$_3$)$_2$ to NiO was replaced by direct temperature programmed H$_2$ reduction of the Ni(NO$_3$)$_2$ as described by Bartholomew and Farrauto (1976). The % Ni loading of the catalyst was defined as the weight ratio of Ni to the combined weight of ZSM-5+Al$_2$O$_3$ times 100.

Reaction Product Analysis

Reaction products were determined by on-line gas chromatography (GC) using a 30 meter megabore (0.53 Mm) GS-Q column operated in a temperature programmed mode over a temperature range of 70°-236° C. and helium carrier gas flow rate of 8 ml/min. FID detection was employed. Using this system, excellent separations were obtained for low molecular weight hydrocarbons up through C$_{11}$. In addition, possible partially dechlorinated intermediates (e.g., dichloroethylenes, vinyl chloride) were well resolved and easily identified in the presence of a complex hydrocarbon mixture. Hydrocarbon products and GC response factors were obtained by calibrations with known pure compounds. A Varian Model 4400 integrator was used to compute and record peak areas. Reaction product distributions were reported in terms of product selectivity expressed relative to carbon atom number.

Chlorine and Hydrogen Chloride Analysis

A number of experiments were carried out in which the catalyst exhaust gases were analyzed for chlorine and hydrogen chloride content. Molecular chlorine was determined by bubbling the exhaust gases through 0.1 M KI solution and then measuring any iodine formed by Cl$_2$ Oxidation via an iodometric titration for liberated I$_2$. Hydrogen chloride analysis of the catalyst exhaust was achieved by allowing these gases to bubble through a 0.01 M NaOH solution containing 1.5% hydrogen peroxide. Any Cl$_2$ present in the exhaust gas would be converted to chloride ion via the reaction:

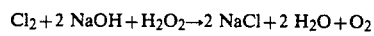

$$Cl_2 + 2\ NaOH + H_2O_2 \rightarrow 2\ NaCl + 2\ H_2O + O_2$$

The total chloride in the solution was determined spectrophotometrically by complex formation with mercury(II) thiocyanate. The HCl in the exhaust gas was calculated by first subtracting the chloride contribution from Cl$_2$ as determined iodometrically. Negligible chlorine content in the exhaust gas was found; therefore, the total extent of the spectrophotometric complex formation was attributed to the HCl content of the exhaust gases. Under none of the reaction conditions employed in this work was molecular chlorine found as a reaction product. Typically, large amounts of chlorine representing at least 97% of the total theoretically available chlorine under reaction conditions of complete dechlorination of starting material were found.

EXAMPLE 1

The following example illustrates that a polychlorinated hydrocarbon undergoes complete removal of chlorine under the reaction conditions described. In this example, trichloroethylene is used as an example of a multichlorinated substrate.

Hydrodechlorination of Trichloroethylene

A feedstream containing trichloroethylene and hydrogen was fed over a 10% Ni/H-ZSM-5/Al$_2$O$_3$ catalyst at a reaction temperature of 425° C. The trichloroethylene GHSV was 1260 hr$^{-1}$. Hydrocarbon product distribution as a function of time onstream obtained in continuous conversion is shown in FIG. 1. No chlorinated hydrocarbons were identified in the product. Product paraffins were measured initially at about 70%, decreasing to about 50% after 9-10 hrs. The remaining products were aromatics and olefins. Yield of olefins was negligible. Conversion of trichloroethylene was 100%.

EXAMPLE 2

This example illustrates removal of chlorine from a trichlorinated aliphatic hydrocarbon.

Hydrodechlorination of 1,1,2-trichloroethane

A feedstock of 1,1,2-trichloroethane and hydrogen was fed over a nickel-loaded (10% by weight) ZSM-5 catalyst over a period of 11 hrs. Table I shows variations in product distribution with time onstream at 350° C. at a H$_2$/TCA ratio of 6:1. Table II illustrates product distribution under the same conditions except that the H$_2$/TCA ratio was reduced to 3:1. Table III illustrates the effect of increasing the temperature to 450° C. at a H$_2$/TCA ratio of 3:1. In these tables, product selectivities are expressed in terms of carbon atom numbers (taking into account the number of carbon atoms per product molecule) and have been normalized to 100% with respect to carbon atom distribution among the pure hydrocarbon products.

Complete conversion of TCA at temperatures above 350° C. was achieved without the formation of chlorinated hydrocarbon byproducts. As shown in Table I, it was possible to maintain 100% dechlorination of 1,1,2-TCA for 11 hrs at 350° C. at a H$_2$ to TCA reactant ratio of 6:1 and a space velocity of 1260 hr$^{-1}$. Under these conditions, paraffin formation is strongly favored.

Continued catalytic conversion of the 1,1,2-TCA was achieved and maintained for an approximate 9-hr. period even when the H$_2$/TCA reactant ratio was reduced to 3:1 (Table II). In these experiments, helium was substituted as make-up gas to compensate for the decreased flow of H$_2$ and thus provide a constant space velocity of 1260 hr$^{-1}$. Two major trends were noticeable in comparing data from the experiments at H$_2$/TCA reactant ratios of 6:1 (Table I) and 3:1 (Table II). The first difference was that although 100% conversion of the 1,1,2-TCA is maintained in both experiments over the 11-hr period involved, complete dechlorination was lost during the latter stages of the run at reduced H$_2$ flow. This is shown in Table II after 9 and 11 hrs. of time on-stream where measurable amounts of dichloro- and monochloroethylene were detected in the product stream for the first time. The second notable difference in contrasting data in Tables I and II was a substantial difference in hydrocarbon product distributions, especially with respect to decreased paraffin and increased aromatic formation at the lower H$_2$/TCA reactant ratio.

TABLE I

Variations in Product Distributions with Time On-Stream (TOS) in the Conversion of 1,1,2-Trichloroethane (TCA) at 350° C. and a H$_2$/TCA Ratio of 6:1

| TOS (Hr): | 1.0 | 2.5 | 4.5 | 8.0 | 11.0 |
|---|---|---|---|---|---|
| Conversion (%): | 100.0 | 100.0 | 100.0 | 100.0 | 100.0 |
| Product Distribution | | | | | |
| Chlorinated Hydrocarbon | 0.0 | 0.0 | 0.0 | 0.0 | 0.0 |
| Hydrocarbon | 100.0 | 100.0 | 100.0 | 100.0 | 100.0 |
| Hydrocarbon Distribution | | | | | |
| Olefins | | | | | |
| C$_2$ | 0.4 | 0.3 | 0.2 | 0.2 | 0.3 |
| C$_3$ | 0.1 | 0.0 | 0.0 | 0.0 | 0.0 |
| C$_4$ | 0.0 | 0.0 | 0.0 | 0.0 | 0.0 |
| Selectivity | 0.5 | 0.3 | 0.2 | 0.2 | 0.3 |
| Paraffins | | | | | |
| C$_1$ | 8.9 | 7.2 | 7.7 | 8.5 | 8.9 |
| C$_2$ | 18.4 | 16.4 | 13.6 | 14.2 | 15.3 |
| C$_3$ | 36.0 | 41.3 | 4.0 | 40.9 | 40.4 |
| C$_4$ | 6.5 | 5.2 | 4.4 | 4.6 | 4.6 |
| C$_{5+}$ | 0.1 | 0.0 | 0.1 | 0.0 | 0.1 |
| Selectivity | 69.9 | 70.1 | 66.8 | 68.2 | 69.2 |
| Aromatics | | | | | |
| Benzene | 7.2 | 9.9 | 10.6 | 10.5 | 10.6 |
| Toluene | 10.5 | 13.7 | 15.1 | 14.1 | 13.8 |
| C$_8$ | 3.7 | 5.3 | 5.8 | 5.0 | 4.7 |
| C$_9$ | 1.0 | 0.5 | 0.6 | 0.8 | 0.3 |
| C$_{10}$ + C$_{11}$ | 7.2 | 0.9 | 0.9 | 1.2 | 1.0 |
| Selectivity | 29.6 | 30.6 | 33.0 | 31.6 | 30.4 |

NOTE: Reactor Conditions: Wt. of Catalyst = 400 mg; [H$_2$]/[TCA] = 6/1; Space Velocity = 1260 hr$^1$; % Nickel Loading of Catalyst = 10% by weight.

TABLE II

Variations in Product Distributions with Time On-Stream in the Conversion of 1,1,2-TCA at 350° C. Under a Reduced Hydrogen Flow [H$_2$/He/TCA = 3/3/1]

| TOS (hr): | 1.0 | 2.0 | 3.0 | 4.5 | 6.5 | 9.0 | 11.0 |
|---|---|---|---|---|---|---|---|
| Conversion (%): | 100.0 | 100.0 | 100.0 | 100.0 | 100.0 | 100.0 | 100.0 |
| Product Distribution | | | | | | | |
| trans-1,2-Dichloroethylene | 0.0 | 0.0 | 0.0 | 0.0 | 0.0 | 3.3 | 11.3 |
| cis-1,2-Dichloroethylene | 0.0 | 0.0 | 0.0 | 0.0 | 0.0 | 3.9 | 18.0 |
| Vinyl chloride | 0.0 | 0.0 | 0.0 | 0.0 | 0.0 | 0.1 | 0.7 |
| Hydrocarbon | 100.0 | 100.0 | 100.0 | 100.0 | 100.0 | 92.7 | 70.0 |
| Hydrocarbon Distribution | | | | | | | |
| Olefins | | | | | | | |
| C$_2$ | 0.7 | 0.8 | 1.1 | 1.3 | 1.9 | 3.2 | 7.6 |
| C$_3$ | 0.6 | 0.6 | 1.0 | 1.2 | 1.9 | 6.5 | 8.1 |
| n + i-C$_4$ | 0.0 | 0.0 | 0.0 | 0.0 | 1.1 | 2.4 | 4.1 |
| 2-C$_4$ | 0.0 | 0.0 | 0.0 | 0.0 | 0.0 | 1.2 | 3.4 |
| Selectivity | 1.3 | 1.4 | 2.1 | 2.5 | 4.9 | 13.3 | 23.2 |
| Paraffins | | | | | | | |
| C$_1$ | 6.6 | 5.4 | 6.2 | 5.9 | 7.1 | 7.6 | 8.1 |
| C$_2$ | 4.5 | 3.3 | 3.7 | 3.0 | 3.0 | 3.1 | 3.1 |
| C$_3$ | 18.6 | 17.7 | 18.0 | 17.7 | 13.9 | 11.0 | 7.7 |
| i-C$_4$ | 13.6 | 11.6 | 12.7 | 12.2 | 10.0 | 8.0 | 5.8 |
| n-C$_4$ | 5.4 | 5.1 | 5.5 | 5.9 | 5.0 | 3.4 | 2.3 |

TABLE II-continued

Variations in Product Distributions with Time On-Stream in the Conversion of
1,1,2-TCA at 350° C. Under a Reduced Hydrogen Flow [$H_2$/He/TCA = 3/3/1]

| | | | | | | | |
|---|---|---|---|---|---|---|---|
| $C_{5+}$ | 3.6 | 3.8 | 4.8 | 5.0 | 5.5 | 4.8 | 4.3 |
| Selectivity | 52.3 | 46.9 | 50.9 | 49.7 | 44.5 | 37.9 | 31.3 |
| Aromatics | | | | | | | |
| Benzene | 5.9 | 6.2 | 5.7 | 5.8 | 5.1 | 4.1 | 2.5 |
| Toluene | 19.9 | 21.7 | 21.0 | 19.4 | 20.4 | 18.3 | 13.8 |
| $C_8$ | 14.5 | 15.4 | 15.4 | 14.5 | 17.6 | 18.4 | 18.8 |
| $C_9$ | 1.7 | 2.8 | 3.0 | 3.4 | 4.1 | 4.8 | 7.2 |
| $C_{10} + C_{11}$ | 4.4 | 5.6 | 3.9 | 4.7 | 3.4 | 3.2 | 3.2 |
| Selectivity | 46.4 | 51.7 | 47.0 | 47.8 | 50.6 | 48.8 | 45.5 |

NOTE: Catalyst and reactor conditions were identical to those in Table I with the exception of a reduced $H_2$ flow and addition of He make-up gas to maintain space velocity.

TABLE III

Variations in Product Distributions with Time On-Stream in the Conversion of
1,1,2-TCA at 450° C. and a $H_2$/TCA Ratio of 3:1

| | | | | | | | |
|---|---|---|---|---|---|---|---|
| TOS (Hr): | 1.0 | 2.0 | 3.0 | 11.0 | 14.0 | 22.0 | 24.0 |
| Conversion (%): | 100.0 | 100.0 | 100.0 | 100.0 | 100.0 | 100.0 | 100.0 |
| Product Distribution | | | | | | | |
| Chlorinated Hydrocarbon | 0.0 | 0.0 | 0.0 | 0.0 | 0.0 | 0.0 | 0.0 |
| Hydrocarbon | 100.0 | 100.0 | 100.0 | 100.0 | 100.0 | 100.0 | 100.0 |
| Hydrocarbon Distribution | | | | | | | |
| Olefins | | | | | | | |
| $C_2$ | 3.7 | 1.6 | 1.2 | 2.3 | 2.3 | 2.5 | 2.6 |
| $C_3$ | 2.0 | 0.3 | 0.3 | 0.5 | 0.8 | 0.9 | 0.9 |
| n + i-$C_4$ | 0.2 | 0.0 | 0.0 | 0.0 | 0.0 | 0.0 | 0.0 |
| 2-$C_4$ | 0.3 | 0.0 | 0.0 | 0.0 | 0.0 | 0.0 | 0.0 |
| Selectivity | 6.2 | 1.9 | 1.5 | 2.8 | 3.1 | 3.4 | 3.5 |
| Paraffins | | | | | | | |
| $C_1$ | 6.2 | 20.3 | 13.8 | 25.0 | 13.3 | 14.9 | 14.8 |
| $C_2$ | 2.1 | 15.5 | 11.0 | 19.8 | 7.2 | 8.3 | 8.5 |
| $C_3$ | 10.3 | 7.2 | 5.8 | 9.8 | 16.7 | 16.3 | 14.7 |
| i-$C_4$ | 1.4 | 0.1 | 0.1 | 0.1 | 0.6 | 0.5 | 0.4 |
| n-$C_4$ | 1.1 | 0.2 | 0.1 | 0.1 | 0.6 | 0.6 | 0.5 |
| $C_{5+}$ | 0.2 | 0.0 | 0.0 | 0.0 | 0.0 | 0.0 | 0.0 |
| Selectivity | 21.3 | 43.3 | 30.8 | 54.8 | 38.4 | 40.6 | 38.9 |
| Aromatics | | | | | | | |
| Benzene | 16.5 | 20.0 | 16.0 | 19.2 | 18.9 | 19.0 | 19.9 |
| Toluene | 29.9 | 12.1 | 8.9 | 9.5 | 19.0 | 17.8 | 18.1 |
| $C_8$ | 14.2 | 9.5 | 6.9 | 1.7 | 5.6 | 4.9 | 4.8 |
| $C_9$ | 11.8 | 13.0 | 26.5 | 0.4 | 1.0 | 0.6 | 0.9 |
| $C_{10} + C_{11}$ | 0.1 | 0.2 | 9.4 | 11.6 | 14.0 | 13.7 | 13.9 |
| Selectivity | 72.5 | 54.8 | 67.7 | 42.4 | 58.5 | 56.0 | 57.6 |

NOTE: Catalyst and reactor conditions were identical to those in TABLE I with the exception of a reduced $H_2$ flow and addition of He make-up gas to maintain space velocity.

Reactions carried out at 450° C. resulted in the conversions and product distributions shown in Table III. Complete conversion and dechlorination of the reactant trichloro-solvent was maintained over the 24-hr period of this experiment. There was a noticeable shift in hydrocarbon product distribution favoring formation of aromatics by comparison with reactions run at 350° C. As shown in Table III, there was a high aromatic yield, favoring monocyclic aromatics, during the initial hour of conversion. Overall, there were significant variations with hydrocarbon product distributions during the first few hours of conversion with a steady-state distribution being achieved at longer reaction times.

EXAMPLE 3

This example illustrates the importance of incorporating elemental nickel in the zeolite catalyst used for the dehydrohalogenation reaction.

1,1,2-Trichloroethane Conversion over H-ZSM-5 Catalyst 1,1,2-Trichloroethane was converted under the same conditions as Example 2 except that a ZSM-5 catalyst was used in place of the nickel-loaded ZSM-5 catalyst. As shown in Table IV, incomplete dechlorination of TCA was obtained even during the initial time onstream. For example, the percentage conversion of the TCA dropped from 100% to 34.4% after only 150 minutes of onstream conversion. Additionally, even during the initial reaction stage, the product distribution consisted overwhelmingly (98%) of chlorine-containing molecules (e.g. dichloroethylenes). Clearly, unmodified H-ZSM-5 is not an effective catalyst for obtaining complete dechlorination of this polyhalogenated reactant.

EXAMPLE 4

This example illustrates the conversion of a multihalogenated aliphatic hydrocarbon over a nickel-containing zeolite catalyst.

TABLE IV

Variations in Conversion Percentages and Product Distributions with Time On-Stream in the Conversion of 1,1,2-Trichloroethane Over a Pure H-ZSM-5 Catalyst (No Added Ni) at 350° C. and 450° C.

| TOS (min) | Temp °C. | % Conversion of 1,1,2-TCA | Product Distribution | | | | |
|---|---|---|---|---|---|---|---|
| | | | trans-1,2-Dichloro-ethylene | cis-1,2-Dichloro-ethylene | 1,1-Dichloro-ethylene | Vinyl Chloride | Hydrocarbon |
| 35 | 350 | 100.0 | 35.7 | 58.9 | 0.1 | 3.5 | 1.8 |
| 70 | 350 | 100.0 | 28.9 | 61.7 | 0.2 | 7.6 | 1.6 |
| 110 | 350 | 71.5 | 21.6 | 61.5 | 0.3 | 15.4 | 1.2 |
| 150 | 350 | 34.4 | 18.2 | 53.8 | 0.5 | 25.2 | 2.3 |
| 230 | 450 | 100.0 | 18.3 | 51.3 | 0.4 | 28.5 | 1.5 |
| 270 | 450 | 100.0 | 16.3 | 46.2 | 0.4 | 35.4 | 1.7 |

Dehydrochlorination of 1,1,1-Trichloroethane 1,1,1-trichloroethane (1,1,1-TCA) was converted using the process of Example 1. 100% conversion to product was obtained at GHSV of 1260 hr$^{-1}$ at 450° C. using a nickel containing ZSM-5 catalyst (20% by weight nickel). Aromatic compound yield was steady over a period of 20 hrs at about 40%. Olefin yield was low, being less than 5% after 20 hrs onstream. Paraffin yield ranged from 50–60%. There was no chlorine present in the products. Conversion of starting material was 100%.

EXAMPLE 5

This example illustrates removal of two chlorine atoms from an aliphatic hydrocarbon using a nickel-containing zeolite catalyst.

Conversion of Methylene Chloride

Figure 3:
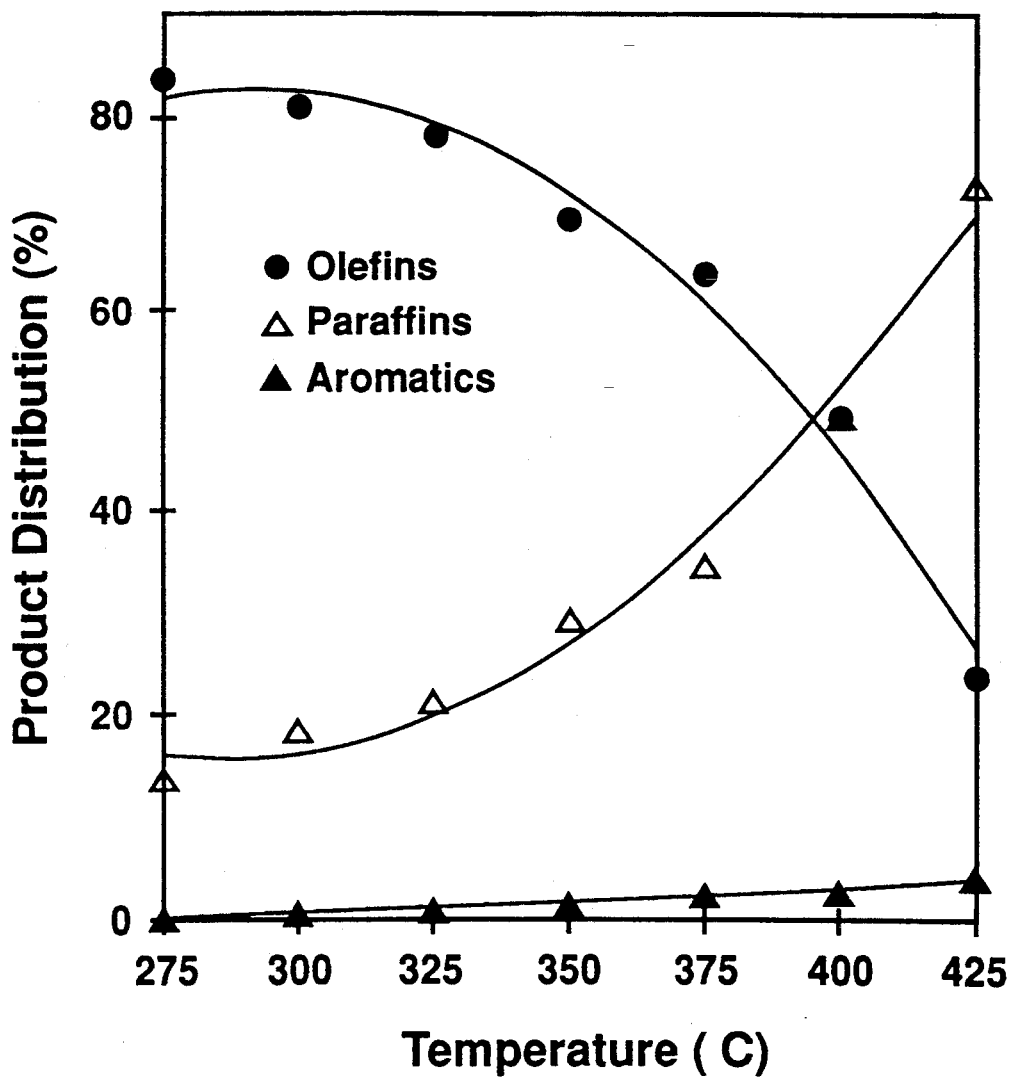
FIG. 3 shows conversion and product distribution for methylene chloride in the presence of methanol over Ni/H-ZSM5/Al$_2$O$_3$, methylene chloride flow was 1.3 ml/min, methanol flow 1.3 ml/min, H$_2$ flow at 12 ml/min, WHSV (MeCl$_2$+MEOH) at 1.7 ml/hr, at 450° C. for 175 min, the lowered to 350° C. Catalyst mass was 600 mg.

Methylene chloride was converted under the same conditions described in Example 2. Results are shown in Table V. A ZSM-5 catalyst containing 10% nickel was used. Small amounts of methyl chloride, less than 4%, were consistently obtained. As shown in Table XV, it is possible to adjust reaction conditions to essentially eliminate $CH_3Cl$ formation in $CH_2Cl_2$ hydrodechlorination. FIG. 3 shows conversion and product distribution for methylene chloride in the presence of hydrogen and methanol.

TABLE V

Ni/H-ZSM-5/$Al_2O_3$ Catalyzed Conversion of $CH_2Cl_2$

| Feed: | | | | | | | | |
|---|---|---|---|---|---|---|---|---|
| $CH_2Cl_2$(ml/min) | 2.3 | 2.3 | 2.3 | 2.3 | 2.3 | 2.3 | 2.3 | 2.3 |
| $H_2$ (ml/min) | 12.0 | 12.0 | 12.0 | 12.0 | 12.0 | 12.0 | 12.0 | 12.0 |
| Time on-stream (min) | 70 | 140 | 220 | 290 | 335 | 370 | 455 | 495 |
| Temperature (°C.) | 450 | 450 | 450 | 450 | 450 | 450 | 450 | 550 |
| WHSV (1/hr)[1] | 1.4 | 1.4 | 1.4 | 1.4 | 1.4 | 1.4 | 1.4 | 1.4 |
| Conversion (%) | 100 | 100 | 100 | 100 | 100 | 100 | 100 | 100 |
| Methyl Chloride (%) | 3.6 | 2.0 | 4.2 | 3.9 | 3.9 | 3.9 | 3.8 | 3.8 |
| Hydrocarbon Distribution (%)[2] | | | | | | | | |
| Olefins | | | | | | | | |
| $C_2$ | 2.2 | 2.5 | 4.2 | 3.8 | 4.6 | 4.1 | 4.8 | 4.5 |
| $C_3$ | 0.0 | 0.0 | 0.0 | 0.0 | 0.0 | 0.0 | 0.0 | 0.0 |
| $C_{4+}$ | 0.0 | 0.0 | 0.0 | 0.0 | 0.0 | 0.0 | 0.0 | 0.0 |
| $C_5$ | 0.0 | 0.0 | 0.0 | 0.0 | 0.0 | 0.0 | 0.0 | 0.0 |
| Selectivity (%) | 2.2 | 2.5 | 4.2 | 3.8 | 4.6 | 4.1 | 4.8 | 4.5 |
| Paraffins | | | | | | | | |
| $C_1$ | 55.4 | 61.0 | 58.2 | 55.3 | 59.4 | 54.3 | 58.7 | 56.7 |
| $C_2$ | 3.8 | 2.7 | 3.1 | 2.5 | 3.0 | 2.6 | 2.8 | 2.6 |
| $C_3$ | 0.3 | 0.2 | 0.8 | 0.8 | 0.9 | 1.0 | 1.1 | 0.9 |
| $C_{4+}$ | 0.0 | 0.0 | 0.0 | 0.0 | 0.0 | 0.0 | 0.0 | 0.0 |
| $C_5$ | 0.0 | 0.0 | 0.0 | 0.0 | 0.0 | 0.0 | 0.0 | 0.0 |
| Selectivity (%) | 59.5 | 63.9 | 62.1 | 58.6 | 63.3 | 57.9 | 62.6 | 62.4 |
| Aromatics | | | | | | | | |
| Benzene | 5.7 | 3.8 | 3.0 | 2.5 | 2.4 | 2.3 | 2.0 | 1.9 |
| Toluene | 15.3 | 13.0 | 11.4 | 10.9 | 10.0 | 10.0 | 8.8 | 7.9 |
| Ethylbenzene | 0.0 | 0.0 | 0.0 | 0.0 | 0.0 | 0.0 | 0.0 | 0.0 |
| Xylenes | 9.7 | 11.3 | 10.5 | 14.6 | 10.4 | 15.4 | 11.9 | 13.7 |
| Ethyltoluene | 1.0 | 1.2 | 1.4 | 2.3 | 2.7 | 2.9 | 3.3 | 2.8 |
| Trimethylbenzene | 2.6 | 2.1 | 2.8 | 3.0 | 2.2 | 2.9 | 2.3 | 2.6 |
| Fused-ring aromatics | 0.0 | 0.0 | 0.0 | 0.0 | 0.0 | 0.0 | 0.0 | 0.0 |
| Selectivity (%) | 34.3 | 31.4 | 29.1 | 33.3 | 27.7 | 33.5 | 28.3 | 28.9 |

1. 10% Ni/H-ZSM-5/$Al_2O_3$(H-ZSM-5/$Al_2O_3$ = 40:60, H-ZSM-5 was treated with $HNO_3$ solution); Catalyst mass: 0.400 g.
2. Percentage based on carbon number of compound.

EXAMPLE 6

This examples illustrates the effect of percent nickel loading in the zeolite on complete removal of chlorine from 1,1,1-trichloroethane.

Effect of Nickel Loading of ZSM-5

Table VI shows results of conversion of 1,1,1-TCA in the presence of hydrogen at 4500C over a 3% nickel-loaded ZSM-5 catalyst. Complete chlorine stripping was obtained initially but after approximately 280 minutes onstream, an initial chlorohydrocarbon product (vinyl chloride) was observed and chlorohydrocarbons increased with continued reaction. Table VII illustrates that at 1% nickel loading significant chlorohydrocarbon product was obtained after only 63 minutes time onstream in the conversion of 1,1,2-TCA. At higher nickel loadings, as shown in Tables I and III, no chlorinated hydrocarbon products were observed under the same conditions of reaction.

EXAMPLE 7

This example illustrates the high catalytic activity of the Ni/ZSM-5/Al$_2$O$_3$ catalyst developed as shown by complete dechlorination of 1,1,1-TCA over a wide range of contact times between the reactant and the catalyst.

Effect of High Space Velocities on 1,1,1-TCA Conversion

The effect of space velocities ranging from 17827 to 608 hr$^{-1}$ GHSV on 1,1,1-TCA conversion are shown in Table VIII. Although the accelerated flows decreased the contact time between the reactant and catalyst, the reactant WHSV remained about 0.65$^{-1}$, the same observed with the lesser flow rates used in previous examples. As illustrated by these results, it was clearly possible to obtain complete dechlorination of the 1,1,1-TCA reactant over a wide range of contact times between the reactant and the Ni/ZSM-5/Al$_2$O$_3$ catalyst.

TABLE VII

| 1,1,2 Trichloroethane/H$_2$ over Ni(1%)/HZSM5/Al$_2$O$_3$ at 450° C.[a] | | | | | |
|---|---|---|---|---|---|
| TOS (min): | 63 | 107 | 145 | 275 | 376 |
| Conv. (%): | 100.0 | 100.0 | 100.0 | 100.0 | 100.0 |
| Product Distribution | | | | | |
| TCA | 0.0 | 0.0 | 0.0 | 0.0 | 0.0 |
| 1,1 DCE[a] | 1.0 | 7.1 | 8.8 | 12.3 | 12.5 |
| Vinylchloride | 0.0 | 2.6 | 3.4 | 4.9 | 5.1 |
| Other Chloro Compounds | 0.0 | 0.0 | 0.0 | 0.0 | 0.0 |
| Hydrocarbon | 99.0 | 90.3 | 87.8 | 82.8 | 82.4 |
| Hydrocarbon Distribution | | | | | |
| Olefins | | | | | |
| C$_2$ | 1.5 | 9.0 | 11.1 | 12.9 | 15.9 |
| C$_3$ | 0.5 | 9.4 | 11.4 | 12.1 | 12.6 |
| 1 + i-C$_4$ | 0.0 | 1.4 | 2.1 | 2.0 | 2.8 |
| 2-C$_4$ | 0.0 | 1.4 | 2.3 | 1.8 | 3.2 |
| C$_{5+}$ | 0.0 | 0.3 | 0.9 | 2.5 | 3.6 |
| Selectivity: | 2.0 | 21.5 | 27.8 | 31.3 | 38.1 |
| Paraffins | | | | | |
| C$_1$ | 1.4 | 2.6 | 3.4 | 4.4 | 5.0 |
| C$_2$ | 0.1 | 0.6 | 0.7 | 1.3 | 1.4 |
| C$_3$ | 0.2 | 0.2 | 0.2 | 0.2 | 0.2 |
| C$_{4+}$ | 0.0 | 0.0 | 0.0 | 0.0 | 0.0 |
| Selectivity: | 1.7 | 3.4 | 4.3 | 5.9 | 6.6 |
| Aromatics | | | | | |
| Benzene | 1.7 | 6.5 | 5.9 | 4.8 | 4.5 |
| Toluene | 6.7 | 16.3 | 15.9 | 13.5 | 12.3 |
| C$_8$ | 8.7 | 13.5 | 14.5 | 13.6 | 12.4 |
| C$_9$ | 36.9 | 8.0 | 9.1 | 9.1 | 8.3 |
| C$_{10}$ | 14.1 | 12.0 | 7.2 | 10.4 | 9.1 |
| C$_{11}$ | 27.5 | 18.6 | 15.3 | 11.4 | 8.2 |
| Selectivity: | 95.6 | 74.9 | 67.9 | 62.8 | 54.8 |

[a]TCA = 4.3 mg/min, H$_2$ = 5 ml/min, N$_2$ = 25 ml/min, WHSV = 0.65 hr$^{-1}$, catalyst = 400 mg, DCE = dichloroethylene.

TABLE VI

| 1,1,1 Trichloroethane/H$_2$ over Ni(3%)/HZSM5/Al$_2$O$_3$ at 450° C.[a] | | | | | | | | | |
|---|---|---|---|---|---|---|---|---|---|
| TOS (min): | 76 | 133 | 191 | 283 | 339 | 397 | 508 | 635 | 717 |
| Conv (%): | 100.0 | 100.0 | 100.0 | 100.0 | 100.0 | 100.0 | 100.0 | 100.0 | 100.0 |
| Product Distribution | | | | | | | | | |
| TCA | 0.0 | 0.0 | 0.0 | 0.0 | 0.0 | 0.0 | 0.0 | 0.0 | 0.0 |
| 1,1 DCE[1] | 0.0 | 0.0 | 0.0 | 0.0 | 0.0 | 0.0 | 0.1 | 0.5 | 1.0 |
| Vinylchloride | 0.0 | 0.0 | 0.0 | 0.1 | 0.2 | 0.3 | 0.6 | 1.0 | 1.3 |
| Other chloro compounds | 0.0 | 0.0 | 0.0 | 0.0 | 0.0 | 0.0 | 0.0 | 0.0 | 0.0 |
| Hydrocarbon | 100.0 | 100.0 | 100.0 | 99.9 | 99.8 | 99.7 | 99.3 | 98.5 | 97.7 |
| Hydrocarbon Distribution | | | | | | | | | |
| Olefins | | | | | | | | | |
| C$_2$ | 6.6 | 11.1 | 12.1 | 10.1 | 12.9 | 12.3 | 14.6 | 14.7 | 17.7 |
| C$_3$ | 4.2 | 6.2 | 7.9 | 7.5 | 9.3 | 8.8 | 10.5 | 11.1 | 12.8 |
| 1 + i-C$_4$ | 0.2 | 0.5 | 0.5 | 0.6 | 0.8 | 0.8 | 1.2 | 1.5 | 1.9 |
| 2-C$_4$ | 0.3 | 0.6 | 0.7 | 0.6 | 0.9 | 0.9 | 1.1 | 1.3 | 1.7 |
| C$_{5+}$ | 0.1 | 0.1 | 0.1 | 0.0 | 0.1 | 0.1 | 0.5 | 0.5 | 0.6 |
| Selectivity: | 11.4 | 18.5 | 21.3 | 18.8 | 24.0 | 23.1 | 27.9 | 29.1 | 34.7 |
| Paraffins | | | | | | | | | |
| C$_1$ | 2.6 | 3.8 | 4.1 | 3.5 | 4.5 | 4.4 | 5.5 | 6.2 | 7.7 |
| C$_2$ | 0.6 | 0.9 | 1.0 | 1.0 | 1.0 | 1.0 | 1.2 | 1.7 | 2.1 |
| C$_3$ | 0.3 | 0.1 | 0.5 | 0.1 | 0.1 | 0.1 | 0.1 | 0.1 | 0.2 |
| C$_{4+}$ | 0.0 | 0.0 | 0.0 | 0.0 | 0.0 | 0.0 | 0.0 | 0.0 | 0.0 |
| Selectivity: | 3.5 | 4.8 | 5.6 | 4.6 | 5.6 | 5.5 | 6.8 | 8.0 | 10.0 |
| Aromatics | | | | | | | | | |
| Benzene | 6.4 | 7.6 | 7.4 | 6.7 | 6.7 | 6.3 | 6.1 | 5.8 | 6.2 |
| Toluene | 14.8 | 17.6 | 17.6 | 16.8 | 16.2 | 15.8 | 15.4 | 15.1 | 16.3 |
| C$_8$ | 9.6 | 11.2 | 11.6 | 11.8 | 11.0 | 11.2 | 11.5 | 12.2 | 11.5 |
| C$_9$ | 3.2 | 3.0 | 3.4 | 4.5 | 4.3 | 5.0 | 5.1 | 5.9 | 4.6 |
| C$_{10}$ | 18.1 | 13.1 | 11.4 | 14.1 | 12.2 | 12.6 | 11.2 | 11.1 | 10.8 |
| C$_{11}$ | 33.0 | 24.2 | 21.7 | 22.7 | 20.0 | 20.5 | 16.0 | 12.8 | 5.9 |
| Selectivity | 85.1 | 76.7 | 73.1 | 76.6 | 70.4 | 71.4 | 65.3 | 62.9 | 55.3 |

[a]TCA = 4.3 mg/min, H$_2$ = 5 ml/min, N$_2$ = 25 ml/min, WHSV = 0.65 hr$^{-1}$, catalyst = 400 mg, DCE = dichloroethylene.

TABLE VIII

| Accelerates Flow Rate Through Catalyst 1,1,1 Trichloroethane/H$_2$ over Ni(5%)/HZSM5/Al$_2$O$_3$ at 450° C.[a] | | | | | | |
|---|---|---|---|---|---|---|
| H$_2$ (ml/min): | 5.0 | 5.0 | 5.0 | 5.0 | 5.0 | 5.0 |
| He (ml/min): | 164 | 95 | 41.4 | 16.8 | 6.1 | 0.0 |
| GHSV (hr$^{-1}$): | 17827 | 10582 | 4954 | 2371 | 1247 | 608 |

TABLE VIII-continued

Accelerates Flow Rate Through Catalyst
1,1,1 Trichloroethane/$H_2$ over Ni(5%)/HZSM5/$Al_2O_3$ at 450° C.[a]

| Conv (%): | 100.0 | 100.0 | 100.0 | 100.0 | 100.0 | 100.0 |
|---|---|---|---|---|---|---|
| Product Distribution | | | | | | |
| Chlorinated Compounds | 0.0 | 0.0 | 0.0 | 0.0 | 0.0 | 0.0 |
| Hydrocarbon | 100.0 | 100.0 | 100.0 | 100.0 | 100.0 | 100.0 |
| Hydrocarbon Distribution | | | | | | |
| Olefins | | | | | | |
| $C_2$ | 7.5 | 10.4 | 10.4 | 10.4 | 7.3 | 4.7 |
| $C_3$ | 5.0 | 7.4 | 6.9 | 7.5 | 6.2 | 4.1 |
| 1 + i-$C_4$ | 0.0 | 0.0 | 0.0 | 0.4 | 0.7 | 0.8 |
| 2-$C_4$ | 0.0 | 0.0 | 0.0 | 0.5 | 1.4 | 1.4 |
| Selectivity: | 12.5 | 17.8 | 17.3 | 18.8 | 15.6 | 11.0 |
| Paraffins | | | | | | |
| $C_1$ | 5.9 | 6.0 | 4.7 | 4.6 | 5.0 | 6.0 |
| $C_2$ | 0.8 | 0.8 | 1.0 | 0.7 | 1.5 | 2.3 |
| $C_3$ | 0.0 | 0.0 | 0.0 | 2.2 | 4.2 | 7.5 |
| i-$C_4$ | 0.0 | 0.0 | 0.0 | 0.0 | 0.4 | 1.9 |
| n-$C_4$ | 0.0 | 0.0 | 0.0 | 0.0 | 0.4 | 1.2 |
| Selectivity: | 6.7 | 6.8 | 5.7 | 7.5 | 11.5 | 18.9 |
| $C_{5+}$-Aliphatics | 0.0 | 0.0 | 0.0 | 0.4 | 1.5 | 1.9 |
| Aromatics | | | | | | |
| Benzene | 10.9 | 9.9 | 8.7 | 8.1 | 7.8 | 7.3 |
| Toluene | 20.0 | 21.2 | 21.2 | 20.8 | 21.2 | 21.5 |
| $C_8$ | 6.0 | 10.8 | 12.8 | 13.7 | 16.8 | 18.3 |
| $C_9$ | 0.0 | 0.0 | 3.9 | 3.1 | 3.8 | 4.6 |
| $C_{10}$ | 25.6 | 16.8 | 12.7 | 9.9 | 7.3 | 5.4 |
| $C_{11+}$ | 18.3 | 16.7 | 17.7 | 17.7 | 14.5 | 11.1 |
| Selectivity: | 80.8 | 75.4 | 77.0 | 73.3 | 71.4 | 68.2 |

[a]catalyst = 400 mg. TCA = 4.3 mg/min.

EXAMPLE 8

The following are examples of ineffective catalysts with respect to achieving continuous complete dechlorination of polychlorinated reactants as demonstrated with 1,1,1-TCA. These catalysts include pure H-ZSM-5, pure $Al_2O_3$ and a combined Ni/$Al_2O_3$ catalyst.

Effect of Catalyst on 1,1,1-TCA Conversion

Table IX shows that the H-ZSM-5 catalyst underwent rapid deactivation with the initial product mix consisting basically of 1,1-dichloroethylene (54%) and hydrocarbons (44%). With continued time onstream, the hydrocarbon yield dropped rapidly and 1,1-dichloroethylene represented 95% of the products after only 258 minutes time onstream.

Table X shows that pure $Al_2O_3$ catalyst hydrodechlorinated TCA but only to the extent of forming primarily dichloroethylene. With pure $Al_2O_3$ catalyst, the initial low yield of hydrocarbons (16%) decreased rapidly with time onstream.

Table XI shows that whereas a combined Ni/$Al_2O_3$ catalyst exhibited good initial activity for complete chlorine stripping of TCA, this activity lasted only about 1 hr. Subsequently, catalyst deactivation occurred, leading to a decrease in hydrocarbon formation from 100% to 8% after 323 minutes of time onstream.

TABLE IX

No Ni
1,1,1 Trichloroethane/$H_2$ over H-ZSM-5 at 450° C.[a]

| TOS (min) | 10 | 38 | 80 | 150 | 209 | 258 |
|---|---|---|---|---|---|---|
| Conv. (%) | 100.0 | 100.0 | 100.0 | 100.0 | 100.0 | 100.0 |
| Product Distribution | | | | | | |
| 1,1 dichloroethylene | 54.1 | 64.7 | 86.3 | 91.5 | 93.5 | 94.7 |
| cis-1,2 dichloroethylene | 0.5 | 0.9 | 0.3 | 0.1 | 0.1 | 0.1 |
| trans-1,2 dichloroethylene | 0.0 | 0.3 | 0.0 | 0.0 | 0.0 | 0.0 |
| Vinylchloride | 0.0 | 1.9 | 1.9 | 1.5 | 1.3 | 1.4 |
| Other chloro compounds | 1.3 | 0.5 | 0.8 | 0.5 | 0.4 | 0.3 |
| Hydrocarbons | 44.1 | 31.7 | 10.7 | 6.4 | 4.7 | 3.5 |

[a]TCA = 4.3 mg/min, $H_2$ = 5 ml/min, $N_2$ = 25 ml/min, WHSV = 0.65 hr$^{-1}$, catalyst = 400 mg.

TABLE X

Pure $Al_2O_3$ as catalyst. (No Ni or ZSM5)
1,1,1 Trichloroethane/$H_2$ over $Al_2O_3$ at 450° C.[a]

| TOS (min) | 20 | 45 | 82 | 115 | 179 |
|---|---|---|---|---|---|
| Conv. (%) | 100.0 | 100.0 | 100.0 | 100.0 | 100.0 |
| Product Distribution | | | | | |
| 1,1 dichloroethylene | 83.2 | 89.3 | 92.1 | 92.2 | 89.1 |
| cis-1,2 dichloroethylene | 0.0 | 0.0 | 0.0 | 0.0 | 0.0 |
| trans-1,2 dichloroethylene | 0.0 | 0.0 | 0.0 | 0.0 | 0.0 |
| Vinylchloride | 0.2 | 0.3 | 0.8 | 1.6 | 3.7 |
| Other chloro compounds | 0.0 | 0.0 | 0.1 | 0.8 | 3.2 |
| Hydrocarbons | 16.6 | 10.4 | 7.0 | 5.4 | 4.0 |

[a]TCA = 4.3 mg/min, $H_2$ = 5 ml/min, $N_2$ = 25 ml/min, WHSV = 0.65 hr$^{-1}$, catalyst = 400 mg.

TABLE XI

No ZSM-5
1,1,1 Trichloroethane/$H_2$ over Ni(13%)/$Al_2O_3$ at 450° C.[a]

| TOS (min): | 14 | 61 | 98 | 178 | 246 | 299 | 323 |
|---|---|---|---|---|---|---|---|
| Conv. (%) | 100.0 | 100.0 | 100.0 | 100.0 | 100.0 | 98.4 | 94.2 |
| | | Product Distribution | | | | | |
| TCA | 0.0 | 0.0 | 0.0 | 0.0 | 0.0 | 1.6 | 5.8 |
| 1,1 dichloroethylene | 0.0 | 0.1 | 6.0 | 26.1 | 32.8 | 29.4 | 30.3 |
| cis-1,2 dichloroethylene | 0.0 | 0.0 | 0.0 | 0.0 | 16.4 | 32.1 | 33.5 |
| trans-1,2 dichloroethylene | 0.0 | 0.0 | 0.0 | 0.0 | 0.0 | 0.0 | 0.0 |
| Vinylchloride | 0.0 | 0.0 | 0.3 | 2.9 | 1.5 | 1.3 | 1.3 |
| Other Chloro Compounds | 0.0 | 10.2 | 23.0 | 36.2 | 34.6 | 23.0 | 20.4 |
| Hydrocarbons | 100.0 | 89.7 | 70.7 | 34.8 | 14.7 | 12.6 | 8.7 |

[a]TCA = 4.3 mg/min, $H_2$ = 5 ml/min, $N_2$ = 25 ml/min, WHSV = 0.65 $hr^{-1}$, catalyst = 400 mg, DCE = dichloroethylene.

EXAMPLE 9

Effect of Temperature on Conversion Yields

Table XII shows the effect of reaction temperature on the conversion process for trichloroethylene. In order to achieve complete conversion of TCE and negligible chlorinated hydrocarbon products, a minimum reaction temperature of 350° C. or higher is required for the particular WHSV used in these experiments.

Figure 2:
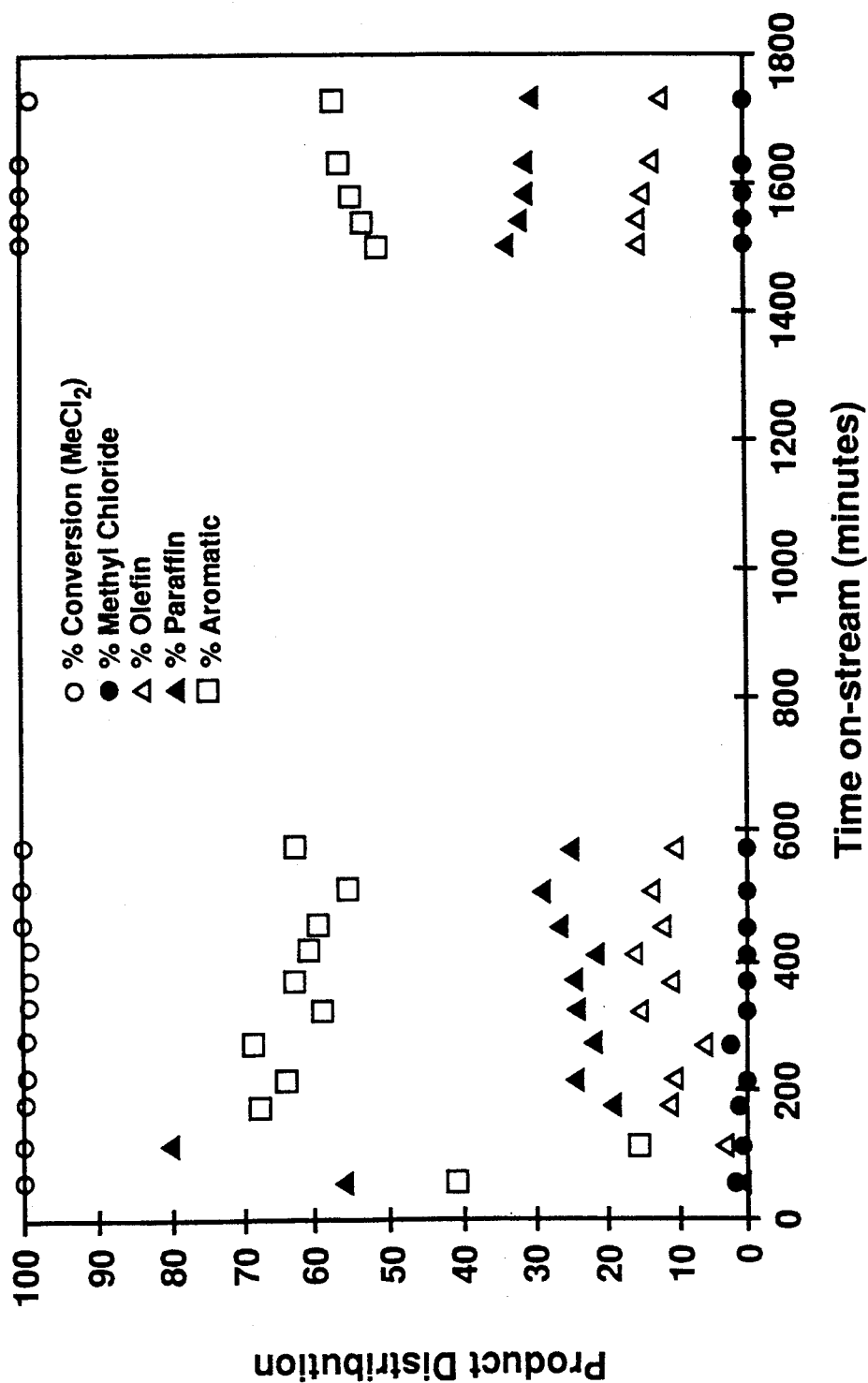
FIG. 2 shows product distribution as a function of reaction temperature in the conversion of 1,1,2-TCA over 10% Ni/ZSM-5/Al$_2$O$_3$ catalyst in the presence of hydrogen and water. Ratio of [H$_2$]/[1,1,2-TCA]=120:1, WHSV (TCA)=0.3 hr-1.

Product distribution as a function of reaction temperature in the conversion of 1,1,2-TCA is shown in FIG. 2 under conditions of a high ratio of [$H_2$] to [TCA] of 120:1. Product distribution is affected by the addition of water to the TCA/$H_2$ feedstream. There is an exceptionally high yield of aromatic products, at temperatures below 400° C., exceeding 70% when the reaction is run at 350° C. at lower of [$H_2$] to [TCA] as shown in Table II.

EXAMPLE 10

The following example illustrates the long-term catalytic stability and effectiveness of the Ni/ZSM-5/$Al_2O_3$ catalyst in promoting complete hydrodechlorination of polyhalogenated reactants. In this run, conducted over an elapsed time of 162 continuous hours, the reaction temperature was cycled over the range of 425° C. to 300° C. Additionally, the reactant ratio of 1,1,2-TCA to $H_2$ was varied. Good reproducibility of product distributions was noted even after long periods of on-stream conversion. The conversions were carried out at relatively high molar ratios of $H_2$ to 1,1,2-TCA thus limiting the yield of aromatics observed among the products. The reaction was terminated after 162 consecutive hours of conversion at which point the catalyst was still providing loot dechlorination of the starting 1,1,2-TCA reactant. The results from this extended conversion reaction are summarized in Table XIII.

TABLE XII

Trichloroethylene over Ni(10%)/H-ZSM-5(1)

| Temperature (°C.): | 250 | 300 | 350 | 400 | 450 |
|---|---|---|---|---|---|
| Conv. (%): | 12.3 | 50.0 | 98.4 | 100.0 | 100.0 |
| | Product Distribution | | | | |
| Chlorinated Hydrocarbon | 14.5 | 2.1 | 0.2 | 0.1 | 0.0 |
| Hydrocarbon | 85.5 | 97.9 | 99.8 | 99.9 | 100.0 |
| | Hydrocarbon Distribution | | | | |
| Acetylene | 9.2 | 2.7 | 0.5 | 1.1 | 2.7 |
| $C_{5+}$ | 0.6 | 1.0 | 0.3 | 0.4 | 0.9 |
| Aliphatics | | | | | |
| Olefins | | | | | |
| $C_2$ | 15.3 | 14.6 | 11.3 | 15.0 | 20.2 |
| $C_3$ | 0.5 | 0.3 | 0.2 | 0.4 | 0.4 |
| $C_4$ | 0.0 | 0.0 | 0.0 | 0.0 | 0.9 |
| Selectivity: | 15.8 | 14.9 | 11.5 | 15.4 | 20.6 |
| Paraffins | | | | | |
| $C_2$ | 18.5 | 8.7 | 5.8 | 10.7 | 13.3 |
| $C_3$ | 16.2 | 25.3 | 28.3 | 30.8 | 14.1 |
| i-butane | 8.8 | 6.7 | 3.6 | 2.6 | 0.6 |
| n-butane | 6.8 | 5.1 | 2.3 | 1.6 | 0.4 |
| Selectivity: | 75.3 | 45.8 | 40.0 | 45.7 | 28.4 |
| Aromatics | | | | | |
| Benzene | 0.0 | 1.7 | 7.8 | 10.3 | 17.9 |
| Toluene | 0.8 | 6.3 | 18.5 | 14.5 | 17.9 |
| $C_8$ | 2.3 | 9.9 | 12.6 | 6.0 | 3.6 |
| $C_9$ | 3.3 | 6.1 | 2.9 | 1.0 | 0.7 |
| $C_{10+}$ | 3.2 | 11.6 | 5.9 | 5.6 | 6.1 |
| Selectivity: | 9.6 | 35.6 | 47.7 | 37.4 | 47.4 |

Condition: TCE = 4.7 mg/min, $H_2$ = 12 ml/min, WHSV = 0.70 $hr^{-1}$, catalyst = 400 mg.
Percentage based on carbon number and 1 hr on stream.

TABLE XIII 1,1,1 Trichloroethane/$H_2$ over Ni(10%)/HZSM5 at 450° C.[a]

| TOS (min): | 30 | 71 | 124 | 180 | 233 | 329 | 385 | 441 | 481 |
|---|---|---|---|---|---|---|---|---|---|
| Conv (%): | 100.0 | 100.0 | 100.0 | 100.0 | 100.0 | 100.0 | 100.0 | 100.0 | 100.0 |
| | | | Product Distribution | | | | | | |
| TCA | 0.0 | 0.0 | 0.0 | 0.0 | 0.0 | 0.0 | 0.0 | 0.0 | 0.0 |
| 1,1 DCE[1] | 0.0 | 0.0 | 0.0 | 0.0 | 0.0 | 0.0 | 0.3 | 8.9 | 26.1 |
| Vinylchloride | 0.0 | 0.0 | 0.0 | 0.0 | 0.0 | 0.0 | 0.0 | 1.4 | 6.8 |
| Other chloro compounds | 0.0 | 0.0 | 0.0 | 0.0 | 0.0 | 0.0 | 0.0 | 0.3 | 2.4 |
| Hydrocarbon | 100.0 | 100.0 | 100.0 | 100.0 | 100.0 | 100.0 | 99.7 | 89.4 | 64.7 |
| | | | Hydrocarbon Distribution | | | | | | |
| Olefins | | | | | | | | | |
| $C_2$ | 6.3 | 8.9 | 10.1 | 10.5 | 11.5 | 12.9 | 13.8 | 15.1 | 17.6 |
| $C_3$ | 2.5 | 3.7 | 4.5 | 4.8 | 5.5 | 6.8 | 6.7 | 10.0 | 11.0 |
| 1 + i-$C_4$ | 0.0 | 0.2 | 0.0 | 0.1 | 0.5 | 0.5 | 0.5 | 0.8 | 1.4 |
| 2-$C_4$ | 0.1 | 0.3 | 0.1 | 0.1 | 0.7 | 0.5 | 0.6 | 0.9 | 1.5 |
| $C_{5+}$ | 0.0 | 0.0 | 0.0 | 0.0 | 0.0 | 0.0 | 0.2 | 0.5 | 0.4 |
| Selectivity: | 8.9 | 13.1 | 14.7 | 15.5 | 18.2 | 20.7 | 21.8 | 27.3 | 31.9 |
| Paraffins | | | | | | | | | |
| $C_1$ | 12.5 | 14.7 | 16.4 | 15.6 | 17.8 | 19.5 | 20.9 | 23.0 | 23.7 |

TABLE XIII-continued

1,1,1 Trichloroethane/$H_2$ over Ni(10%)/HZSM5 at 450° C.[a]

| | | | | | | | | | |
|---|---|---|---|---|---|---|---|---|---|
| $C_2$ | 1.9 | 1.7 | 1.8 | 1.6 | 1.7 | 1.7 | 1.6 | 1.9 | 2.4 |
| $C_3$ | 2.0 | 2.2 | 2.1 | 1.9 | 1.8 | 1.2 | 0.1 | 0.6 | 0.7 |
| $C_{4+}$ | 0.0 | 0.0 | 0.0 | 0.0 | 0.0 | 0.0 | 0.0 | 0.0 | 0.6 |
| Selectivity: | 16.4 | 18.6 | 20.3 | 19.1 | 21.3 | 22.4 | 22.6 | 25.5 | 27.4 |
| Aromatics | | | | | | | | | |
| Benzene | 11.5 | 10.6 | 10.1 | 9.7 | 9.1 | 8.3 | 8.1 | 6.8 | 6.2 |
| Toluene | 18.4 | 17.5 | 17.1 | 17.0 | 16.3 | 15.7 | 14.9 | 13.5 | 12.4 |
| $C_8$ | 7.9 | 7.7 | 7.7 | 8.0 | 7.8 | 7.6 | 7.4 | 7.9 | 7.9 |
| $C_9$ | 1.1 | 1.1 | 1.3 | 1.7 | 1.9 | 1.5 | 3.3 | 3.3 | 3.6 |
| $C_{10}$ | 15.3 | 12.6 | 11.4 | 10.9 | 9.5 | 8.8 | 8.5 | 6.3 | 5.0 |
| $C_{11+}$ | 20.5 | 18.8 | 17.4 | 18.1 | 15.9 | 15.0 | 13.4 | 9.4 | 5.6 |
| Selectivity: | 74.7 | 68.3 | 65.0 | 65.4 | 60.5 | 56.9 | 55.6 | 47.2 | 40.7 |

[a]TCA = 4.3 mg/min, $H_2$ = 5 ml/min, $N_2$ = 25 ml/min, WHSV = 0.65 hr$^{-1}$, catalyst = 400 mg, DCE = dichlorethylene.

EXAMPLE 11

The following examples illustrate that the hydrodechlorination process developed continued to operate effectively even when conversions of the polyhalogenated reactants were carried out in the presence of added reactants such as water and methanol.

Table XIV represents the reaction carried out using a reactant mixture of 1,1,1-TCA, water and hydrogen. Complete dechlorination was obtained with respect to reaction products. The product distribution was similar to that observed with TCA/$H_2$ mixtures (compare Table I), indicating that the presence of $H_2O$ had relatively little effect on product distributions when $H_2$ was present in sufficient concentration.

Tables XV and XVI show data obtained in reactions of equimolar amounts of methylene chloride and methanol in the presence of hydrogen. The conversion was initiated at 450° C. and carried out for approximately 27 hrs at that temperature (Table XV). Subsequently, the temperature was lowered at this point, with the conversion efficiency remaining near 100%. Essentially complete chlorine atom stripping was observed at both temperatures with only minor amounts of methyl chloride noted. The product distribution for $CH_2Cl_2/CH_3OH/H_2$ at 450° C. (Table XV) was similar to that observed with $CH_2Cl_2/H_2$ reactant mixtures at 450° C. (Table XVI). Decreasing the conversion temperature to 400° C. resulted in a sharp change in product distribution for this system (compare data in Tables XV and XVI). At 400° C., a much higher aromatic yield was obtained (particularly for $C_9$ compounds) with a sharp decrease in methane yield.

Table XVII illustrates conversion of $CH_2Cl_2$ with added $CH_3OH$ in which the reaction was initiated at 450° C. with subsequent lowering of the temperature to 350° C. Complete conversion of $CH_2Cl_2$ was obtained with essentially no chlorohydrocarbon byproducts produced. FIG. 3 shows product distribution with time onstream.

TABLE XIV

1,1,1 Trichloroethane/$H_2O$/$H_2$ over Ni(20%)/HZSM5 + $Al_2O_3$ at 450° C.[a]

| | | | | | | | | |
|---|---|---|---|---|---|---|---|---|
| TOS (min): | 60 | 145 | 183 | 255 | 312 | 374 | 430 | 483 |
| Conv (%): | 100.0 | 100.0 | 100.0 | 100.0 | 100.0 | 100.0 | 100.0 | 100.0 |
| Product Distribution | | | | | | | | |
| Chlorinated Hydrocarbon | 0.0 | 0.0 | 0.0 | 0.0 | 0.0 | 0.0 | 0.0 | 0.0 |
| Hydrocarbon | 100.0 | 100.0 | 100.0 | 100.0 | 100.0 | 100.0 | 100.0 | 100.0 |
| Hydrocarbon Distribution | | | | | | | | |
| Olefins | | | | | | | | |
| $C_2$ | 0.7 | 1.4 | 1.6 | 4.2 | 4.8 | 6.4 | 11.5 | 14.9 |
| $C_3$ | 0.5 | 0.8 | 1.0 | 4.6 | 3.6 | 4.6 | 8.3 | 8.0 |
| 1 + i-$C_4$ | 0.0 | 0.0 | 0.0 | 0.0 | 0.0 | 0.0 | 1.4 | 0.6 |
| 2-$C_4$ | 0.0 | 0.0 | 0.0 | 0.0 | 0.0 | 0.0 | 1.5 | 0.7 |
| Selectivity: | 1.2 | 2.2 | 2.6 | 8.8 | 8.4 | 11.0 | 22.7 | 24.2 |
| Paraffins | | | | | | | | |
| $C_1$ | 35.0 | 27.5 | 30.2 | 25.0 | 23.0 | 21.9 | 17.7 | 17.6 |
| $C_2$ | 5.4 | 5.0 | 5.1 | 5.0 | 4.0 | 4.0 | 3.6 | 3.7 |
| $C_3$ | 0.7 | 0.3 | 0.3 | 0.0 | 0.0 | 0.0 | 0.2 | 0.0 |
| i-$C_4$ | 0.0 | 0.0 | 0.0 | 0.0 | 0.0 | 0.0 | 0.0 | 0.0 |
| n-$C_4$ | 0.0 | 0.0 | 0.0 | 0.0 | 0.0 | 0.0 | 0.0 | 0.0 |
| Selectivity: | 41.1 | 32.8 | 35.6 | 30.0 | 27.0 | 25.9 | 21.5 | 21.3 |
| $C_{5+}$- Aliphatics | 0.0 | 0.7 | 1.1 | 1.2 | 4.0 | 1.8 | 1.5 | 0.6 |
| Aromatics | | | | | | | | |
| Benzene | 14.7 | 13.8 | 12.9 | 11.6 | 9.9 | 8.5 | 7.5 | 8.7 |
| Toluene | 19.9 | 20.2 | 18.7 | 17.6 | 14.8 | 13.3 | 13.0 | 14.3 |
| $C_8$ | 6.9 | 7.4 | 6.9 | 6.5 | 5.9 | 5.6 | 6.0 | 6.6 |
| $C_9$ | 0.0 | 0.0 | 0.0 | 0.0 | 0.0 | 0.0 | 1.6 | 1.5 |
| $C_{10+}$ | 16.2 | 22.9 | 22.2 | 24.3 | 30.0 | 33.9 | 26.2 | 22.8 |
| Selectivity: | 57.7 | 64.3 | 60.7 | 60.0 | 60.6 | 61.3 | 54.3 | 53.9 |

TCA = 4.3 mg/min, $H_2$ = 5 ml/min, $H_2O$ = 2.9 mg/min, $N_2$ = 25 ml/min, WHSV = 0.65 hr$^{-1}$ Catalyst = 400 mg.

TABLE XV

Ni/H-ZSM-5/$Al_2O_3$ Catalyzed Conversion of $CH_3OH$/$CH_2Cl_2$

| Feed: | | | | | | | | |
|---|---|---|---|---|---|---|---|---|
| $CH_3OH$ (ml/min) | 2.0 | 2.0 | 2.0 | 2.0 | 2.0 | 2.0 | 2.0 | 2.0 |

TABLE XV-continued

Ni/H-ZSM-5/Al$_2$O$_3$ Catalyzed Conversion of CH$_3$OH/CH$_2$Cl$_2$

| | | | | | | | | |
|---|---|---|---|---|---|---|---|---|
| CH$_2$Cl$_2$ (ml/min) | 2.0 | 2.0 | 2.0 | 2.0 | 2.0 | 2.0 | 2.0 | 2.0 |
| H$_2$ (ml/min) | 12.0 | 12.0 | 12.0 | 12.0 | 12.0 | 12.0 | 12.0 | 12.0 |
| Time on-stream (min) | 310 | 350 | 420 | 460 | 505 | 1505 | 1550 | 1600 |
| Temperature (°C.) | 450 | 450 | 450 | 450 | 450 | 450 | 450 | 450 |
| WHSV (1/hr)[1] | 2.7 | 2.7 | 2.7 | 2.7 | 2.7 | 2.7 | 2.7 | 2.7 |
| Conversion (%)[2] | 100 | 100 | 100 | 100 | 100 | 99.8 | 99.8 | 99.7 |
| Methyl Chloride (%) | 0.0 | 0.0 | 0.0 | 0.0 | 0.0 | 0.9 | 0.9 | 0.8 |
| Methanol (%) | 1.1 | 0.0 | 0.3 | 0.0 | 0.0 | 0.0 | 0.0 | 0.0 |
| Hydrocarbon Distribution (%)[3] | | | | | | | | |
| Olefins | | | | | | | | |
| C$_2$ | 1.4 | 1.6 | 1.4 | 1.8 | 1.7 | 3.5 | 3.2 | 3.0 |
| C$_3$ | 0.0 | 0.0 | 0.0 | 0.0 | 0.0 | 0.0 | 0.0 | 0.0 |
| C$_{4+}$ | 0.0 | 0.0 | 0.0 | 0.0 | 0.0 | 0.1 | 0.1 | 0.1 |
| C$_5$ | 0.0 | 0.0 | 0.0 | 0.0 | 0.0 | 0.0 | 0.0 | 0.0 |
| Selectivity (%) | 1.4 | 1.6 | 1.4 | 1.8 | 1.7 | 3.6 | 3.3 | 3.1 |
| Paraffins | | | | | | | | |
| C$_1$ | 67.9 | 74.7 | 81.4 | 80.2 | 80.2 | 75.2 | 76.8 | 77.2 |
| C$_2$ | 0.9 | 1.1 | 1.3 | 1.4 | 1.3 | 2.2 | 2.2 | 2.3 |
| C$_3$ | 0.0 | 0.0 | 0.0 | 0.0 | 0.0 | 1.0 | 0.9 | 0.8 |
| C$_{4+}$ | 0.0 | 0.0 | 0.0 | 0.0 | 0.0 | 0.0 | 0.0 | 0.0 |
| C$_5$ | 0.0 | 0.0 | 0.0 | 0.0 | 0.0 | 0.0 | 0.0 | 0.0 |
| Selectivity (%) | 68.8 | 75.8 | 82.7 | 81.6 | 81.5 | 78.4 | 79.9 | 80.3 |
| Aromatics | | | | | | | | |
| Benzene | 0.7 | 0.8 | 1.1 | 1.0 | 1.0 | 1.4 | 1.6 | 1.9 |
| Toluene | 8.3 | 4.2 | 4.6 | 4.4 | 4.4 | 4.4 | 4.2 | 4.5 |
| Ethylbenzene | 0.0 | 0.0 | 0.0 | 0.0 | 0.0 | 0.0 | 0.0 | 0.0 |
| Xylenes | 10.5 | 7.2 | 5.9 | 6.4 | 6.7 | 7.2 | 6.4 | 6.0 |
| Ethyltoluene | 1.6 | 1.3 | 1.0 | 1.0 | 1.1 | 0.9 | 0.8 | 0.6 |
| Trimethylbenzene | 4.9 | 3.7 | 2.5 | 2.9 | 3.0 | 2.5 | 2.0 | 1.5 |
| Fused-ring aromatics | 2.7 | 5.4 | 0.9 | 0.8 | 0.6 | 0.7 | 0.6 | 1.0 |
| Selectivity (%) | 28.7 | 22.6 | 15.9 | 16.5 | 16.8 | 16.7 | 15.6 | 15.5 |

[1] 10% Ni/H-ZSM-5/Al$_2$O$_3$(H-ZSM-5/Al$_2$O$_3$ = 40:60, H-ZSM-5 was treated with HNO$_3$ solution): Catalyst mass: 0.600 g. WHSV calculated from weight of MeOH + MeCl$_2$ in flow.
[2] Percent conversion indicates conversion of Methylene Chloride.
[3] Percentage based on carbon number of compound.

TABLE XVI

Ni/H-ZSM-5/Al$_2$O$_3$ Catalyzed Conversion of CH$_3$OH/CH$_2$Cl$_2$

| Feed: | | | |
|---|---|---|---|
| CH$_3$OH (ml/min) | 2.0 | 2.0 | 2.0 |
| CH$_2$Cl$_2$ (ml/min) | 2.0 | 2.0 | 2.0 |
| H$_2$ (ml/min) | 12.0 | 12.0 | 12.0 |
| Time on-stream (min)[1] | 0.0 | 50.0 | 90.0 |
| Temperature (°C.)[1] | 400 | 400 | 400 |
| WHSV (1/hr)[2] | 2.7 | 2.7 | 2.7 |
| Conversion (%)[3] | 98.9 | 98.9 | 99.2 |
| Methyl Chloride (%) | 1.3 | 1.3 | 1.0 |
| Methanol (%) | 0.4 | 0.4 | 0.4 |
| Hydrocarbon Distribution (%)[4] | | | |
| Olefins | | | |
| C$_2$ | 3.5 | 3.7 | 3.4 |
| C$_3$ | 2.0 | 2.2 | 1.5 |
| C$_{4+}$ | 1.8 | 1.9 | 1.3 |
| C$_5$ | 0.0 | 0.0 | 0.0 |
| Selectivity (%) | 7.3 | 7.8 | 6.2 |
| Paraffins | | | |
| C$_1$ | 38.5 | 39.1 | 49.0 |
| C$_2$ | 1.6 | 1.5 | 1.1 |
| C$_3$ | 4.1 | 4.1 | 2.7 |
| C$_{4+}$ | 1.5 | 1.5 | 1.2 |
| C$_5$ | 0.3 | 0.3 | 0.2 |
| Selectivity (%) | 46.0 | 46.5 | 54.2 |
| Aromatics | | | |
| Benzene | 0.6 | 0.5 | 0.4 |
| Toluene | 2.4 | 2.2 | 1.8 |
| Ethylbenzene | 0.0 | 0.0 | 0.0 |
| Xylenes | 11.5 | 10.8 | 9.4 |
| Ethyltoluene | 5.5 | 5.3 | 4.7 |
| Trimethylbenzene | 19.7 | 20.0 | 17.7 |
| Fused-ring aromatics | 4.3 | 4.1 | 3.4 |
| Selectivity (%) | 44.0 | 42.9 | 37.4 |

[1] Time on-stream at 400° C., then at 450° C. for 1600 minutes.
[2] 10% Ni/H-ZSM-5/Al$_2$O$_3$(H-ZSM-5/Al$_2$O$_3$ = 40:60, H-ZSM-5 was treated with HNO$_3$ solution): Catalyst mass: 0.600 g. WHSV calculated from weight of MeOH + MeCl$_2$ in flow.
[3] Percent conversion indicates conversion of Methylene Chloride.
[4] Percentage based on carbon number of compound.

TABLE XVII

Ni/H-ZSM-5/Al$_2$O$_3$ Catalyzed Conversion of CH$_3$OH/CH$_2$Cl$_2$

| Feed: | | | | | | | | |
|---|---|---|---|---|---|---|---|---|
| CH$_3$OH (ml/min) | 1.3 | 1.3 | 1.3 | 1.3 | 1.3 | 1.3 | 1.3 | 1.3 |
| CH$_2$Cl$_2$ (ml/min) | 1.3 | 1.3 | 1.3 | 1.3 | 1.3 | 1.3 | 1.3 | 1.3 |
| H$_2$ (ml/min) | 12.0 | 12.0 | 12.0 | 12.0 | 12.0 | 12.0 | 12.0 | 12.0 |
| Time on-stream (min) | 60 | 115 | 175 | 215 | 270 | 320 | 365 | 410 |
| Temperature (°C.) | 450 | 450 | 350 | 350 | 350 | 350 | 350 | 350 |
| WHSV (1/hr)[1] | 1.7 | 1.7 | 1.7 | 1.7 | 1.7 | 1.7 | 1.7 | 1.7 |
| Conversion (%)[2] | 99.7 | 100 | 99.6 | 99.4 | 99.5 | 99.0 | 99.0 | 98.9 |
| Methyl Chloride (%) | 1.7 | 0.6 | 1.4 | 0.0 | 2.6 | 0.0 | 0.0 | 0.0 |
| Methanol (%) | 0.0 | 0.0 | 0.0 | 0.2 | 0.0 | 0.4 | 0.5 | 0.5 |
| Hydrocarbon Distribution (%)[3] | | | | | | | | |
| Olefins | | | | | | | | |
| C$_2$ | 0.7 | 3.4 | 0.4 | 1.2 | 0.5 | 0.9 | 1.3 | 0.7 |
| C$_3$ | 0.0 | 0.0 | 9.5 | 8.1 | 4.4 | 12.5 | 8.0 | 13.2 |

TABLE XVII-continued

Ni/H-ZSM-5/Al₂O₃ Catalyzed Conversion of CH₃OH/CH₂Cl₂

| | | | | | | | | |
|---|---|---|---|---|---|---|---|---|
| $C_{4+}$ | 0.1 | 0.0 | 1.2 | 1.0 | 1.3 | 1.5 | 1.3 | 1.8 |
| $C_5$ | 0.0 | 0.0 | 0.2 | 0.3 | 0.2 | 0.3 | 0.4 | 0.4 |
| Selectivity (%) | 0.8 | 3.4 | 11.3 | 10.6 | 6.4 | 15.2 | 11.0 | 16.1 |
| Paraffins | | | | | | | | |
| $C_1$ | 55.1 | 74.9 | 16.8 | 12.9 | 14.6 | 13.3 | 10.4 | 12.5 |
| $C_2$ | 1.2 | 0.0 | 1.3 | 0.9 | 1.2 | 1.3 | 0.7 | 1.2 |
| $C_3$ | 0.0 | 5.0 | 0.0 | 8.5 | 4.4 | 7.0 | 11.0 | 5.1 |
| $C_{4+}$ | 0.1 | 0.5 | 1.1 | 1.9 | 1.5 | 2.5 | 2.4 | 2.5 |
| $C_5$ | 0.0 | 0.0 | 0.0 | 0.0 | 0.0 | 0.0 | 0.0 | 0.0 |
| Selectivity (%) | 56.4 | 80.4 | 19.2 | 24.2 | 21.7 | 24.1 | 24.5 | 21.3 |
| Aromatics | | | | | | | | |
| Benzene | 3.1 | 1.4 | 0.2 | 0.2 | 0.2 | 0.4 | 0.3 | 0.4 |
| Toluene | 10.5 | 4.4 | 1.8 | 1.3 | 1.0 | 2.0 | 1.6 | 2.2 |
| Ethylbenzene | 0.0 | 0.0 | 0.0 | 0.0 | 0.0 | 0.0 | 0.0 | 0.0 |
| Xylenes | 13.7 | 3.8 | 12.3 | 11.5 | 8.0 | 12.5 | 13.6 | 13.3 |
| Ethyltoluene | 2.7 | 1.1 | 8.3 | 4.5 | 5.8 | 2.6 | 2.5 | 2.1 |
| Trimethylbenzene | 8.7 | 3.1 | 32.1 | 34.0 | 37.8 | 28.8 | 31.6 | 28.7 |
| Fused-ring aromatics | 2.1 | 1.7 | 13.1 | 12.7 | 16.1 | 13.0 | 13.4 | 14.4 |
| Selectivity (%) | 40.8 | 15.5 | 67.8 | 64.2 | 68.6 | 59.3 | 63.0 | 61.1 |
| Feed: | | | | | | | | |
| CH₃OH (ml/min) | 1.3 | 1.3 | 1.3 | 1.3 | 1.3 | 1.3 | 1.3 | 1.3 |
| CH₂Cl₂ (ml/min) | 1.3 | 1.3 | 1.3 | 1.3 | 1.3 | 1.3 | 1.3 | 1.3 |
| H₂ (ml/min) | 12.0 | 12.0 | 12.0 | 12.0 | 12.0 | 12.0 | 12.0 | 12.0 |
| Time on-stream (min) | 450 | 505 | 570 | 1500 | 1540 | 1580 | 1630 | 1730 |
| Temperature (°C.) | 350 | 350 | 350 | 350 | 350 | 350 | 350 | 350 |
| WHSV (1/hr)[1] | 1.7 | 1.7 | 1.7 | 1.7 | 1.7 | 1.7 | 1.7 | 1.7 |
| Conversion (%)[2] | 100 | 100 | 100 | 100 | 100 | 100 | 100 | 98.9 |
| Methyl Chloride (%) | 0.0 | 0.0 | 0.0 | 0.0 | 0.0 | 0.0 | 0.0 | 0.0 |
| Methanol (%) | 0.5 | 0.5 | 0.3 | 0.0 | 0.0 | 0.0 | 0.0 | 0.0 |
| Hydrocarbon Distribution (%)[3] | | | | | | | | |
| Olefins | | | | | | | | |
| $C_2$ | 1.3 | 1.3 | 1.0 | 1.3 | 1.5 | 1.2 | 1.2 | 1.0 |
| $C_3$ | 8.7 | 9.6 | 7.1 | 11.2 | 11.9 | 10.9 | 9.8 | 8.5 |
| $C_{4+}$ | 1.7 | 2.3 | 2.1 | 2.6 | 1.8 | 2.4 | 2.1 | 2.1 |
| $C_5$ | 0.4 | 0.5 | 0.3 | 0.0 | 0.0 | 0.0 | 0.0 | 0.4 |
| Selectivity (%) | 12.1 | 13.7 | 10.5 | 15.1 | 15.2 | 14.5 | 13.1 | 12.0 |
| Paraffins | | | | | | | | |
| $C_1$ | 11.0 | 11.9 | 14.1 | 29.2 | 28.9 | 25.8 | 26.3 | 25.7 |
| $C_2$ | 0.9 | 0.9 | 0.9 | 0.0 | 0.0 | 0.0 | 0.0 | 0.0 |
| $C_3$ | 11.9 | 12.8 | 7.7 | 3.0 | 2.8 | 2.6 | 2.4 | 2.1 |
| $C_{4+}$ | 2.3 | 2.9 | 1.9 | 1.4 | 0.0 | 2.2 | 2.0 | 1.9 |
| $C_5$ | 0.2 | 0.2 | 0.2 | 0.0 | 0.0 | 0.0 | 0.0 | 0.0 |
| Selectivity (%) | 26.3 | 28.7 | 24.8 | 33.6 | 31.7 | 30.6 | 30.7 | 29.7 |
| Aromatics | | | | | | | | |
| Benzene | 0.6 | 0.6 | 0.2 | 0.0 | 0.0 | 0.0 | 0.0 | 0.2 |
| Toluene | 2.0 | 2.5 | 1.5 | 1.7 | 1.4 | 1.4 | 1.2 | 1.2 |
| Ethylbenzene | 0.0 | 0.0 | 0.0 | 0.0 | 0.0 | 0.0 | 0.0 | 0.0 |
| Xylenes | 15.2 | 15.6 | 12.2 | 6.7 | 6.6 | 6.6 | 6.5 | 10.1 |
| Ethyltoluene | 2.2 | 2.1 | 3.8 | 6.2 | 6.5 | 6.9 | 6.7 | 6.3 |
| Trimethylbenzene | 25.6 | 21.3 | 33.2 | 25.4 | 25.8 | 26.2 | 26.2 | 25.0 |
| Fused-ring aromatics | 14.1 | 13.5 | 12.0 | 11.2 | 12.8 | 13.7 | 15.6 | 14.4 |
| Selectivity (%) | 59.7 | 55.6 | 62.9 | 51.2 | 53.1 | 54.8 | 56.2 | 57.2 |

[1] 10% Ni/H-ZSM-5/Al₂O₃(H-ZSM-5/Al₂O₃ = 40:60, H-ZSM-5 was treated with HNO₃ solution): Catalyst mass: 0.600 g. WHSV calculated from weight of MeOH + MeCl₂ in flow.
[2] Percent conversion indicates conversion of Methylene Chloride.
[3] Percentage based on carbon number of compound.

EXAMPLE 12

This example illustrates the effectiveness of the Ni/H-ZSM-5/Al₂O₃ catalyst in promoting hydrodebromination of bromine containing reactants. The results obtained using 1,2-dibromoethane as reactant are summarized in Table XVIII. Complete 100% conversion of the 1,2,-dibromoethane was maintained over the 8.5 hours of this experiment carried out at 425° C. No bromine-containing organic compounds were detected among the conversion products.

EXAMPLE 13

The following example illustrates the usefulness of the hydrodehalogenation catalyst in achieving complete dechlorination of a perchlorinated (i.e. completely chlorinated) organic reactant as demonstrated in the conversion of tetrachloroethylene. The results obtained in the hydrodechlorination of C₂Cl₄ are shown in Table XIX for experiments conducted at 425° C. Over the 6 hour duration of this experiment, 100% conversion of the C₂Cl₄ was achieved. No chlorinecontaining organic molecules were detected in the reaction products.

EXAMPLE 14

The following example illustrates a complete hydrodehalogenation of a fluorine containing compound. The compound is a typical example of perfluorochloro hydrocarbon similar to environmentally undesirable Freon-type compounds.

TABLE XVIII 1,2 Dibromoethane/H2 over 10% Ni/HZSM5/Al2O3 at 425° C.[a]

| TOS (hr): | 1.0 | 2.0 | 3.0 | 4.0 | 5.0 | 6.0 | 7.0 | 8.5 |
|---|---|---|---|---|---|---|---|---|
| Conv (%): | 100.0 | 100.0 | 100.0 | 100.0 | 100.0 | 100.0 | 100.0 | 100.0 |
| Product Distribution | | | | | | | | |
| Brominated Hydrocarbons | 0.0 | 0.0 | 0.0 | 0.0 | 0.0 | 0.0 | 0.0 | 0.0 |
| Hydrocarbons | 100.0 | 100.0 | 100.0 | 100.0 | 100.0 | 100.0 | 100.0 | 100.0 |
| Hydrocarbon Distribution | | | | | | | | |
| Olefins | | | | | | | | |
| $C_2$ | 40.2 | 41.0 | 43.1 | 42.7 | 46.8 | 45.7 | 46.4 | 51.2 |
| $C_3$ | 13.9 | 14.9 | 15.8 | 15.6 | 17.0 | 15.9 | 16.1 | 16.9 |
| $1 + i\text{-}C_4$ | 1.3 | 1.3 | 1.5 | 1.3 | 0.9 | 0.8 | 0.8 | 0.8 |
| $2\text{-}C_4$ | 2.4 | 2.6 | 2.9 | 2.8 | 2.8 | 2.8 | 2.8 | 2.7 |
| Selectivity | 57.8 | 59.8 | 63.3 | 62.4 | 67.5 | 65.2 | 66.1 | 71.6 |
| Paraffins | | | | | | | | |
| $C_1$ | 3.0 | 3.0 | 3.2 | 3.4 | 3.6 | 3.1 | 2.7 | 2.5 |
| $C_2$ | 9.5 | 9.1 | 8.9 | 8.4 | 8.9 | 8.3 | 8.1 | 8.1 |
| $C_3$ | 4.4 | 4.5 | 4.6 | 4.6 | 4.5 | 4.1 | 4.0 | 3.8 |
| $i\text{-}C_4$ | 1.8 | 1.8 | 1.9 | 1.8 | 1.8 | 1.7 | 1.7 | 1.5 |
| $n\text{-}C_4$ | 1.1 | 1.1 | 1.1 | 1.1 | 1.1 | 0.8 | 0.8 | 0.9 |
| Selectivity | 19.8 | 19.5 | 19.7 | 19.3 | 19.9 | 18.0 | 17.3 | 16.8 |
| $C_5+$ - Aliphatics | 12.4 | 12.4 | 9.5 | 10.7 | 6.7 | 10.1 | 10.2 | 6.4 |
| Aromatics | | | | | | | | |
| Benzene | 1.6 | 1.6 | 1.1 | 1.5 | 1.1 | 1.1 | 1.2 | 0.7 |
| Toluene | 3.5 | 3.0 | 3.0 | 3.0 | 2.7 | 2.8 | 2.5 | 2.1 |
| $C_8$ | 3.2 | 3.1 | 3.0 | 2.9 | 2.8 | 2.6 | 2.4 | 2.2 |
| $C_9+$ | 1.8 | 0.4 | 0.4 | 0.2 | 0.3 | 0.2 | 0.3 | 0.2 |
| Selectivity | 10.1 | 8.1 | 7.5 | 7.6 | 6.9 | 6.7 | 6.4 | 5.2 |

[a]catalyst = 200 mg, 12DBA = 5.0 mg/min, H2 = 15 ml/min, WHSV = 1.5 hr$^{-1}$.

TABLE XIX

Tetrachloroethylene/H2 over 10% Ni/HZSM5/Al2O3 at 425° C.

| TOS (hr): | 2 | 3 | 4 | 5 | 6 |
|---|---|---|---|---|---|
| Conv (%): | 100.0 | 100.0 | 100.0 | 100.0 | 100.0 |
| Product Distribution | | | | | |
| Chlorinated Hydrocarbons | 0.0 | 0.0 | 0.0 | 0.0 | 0.0 |
| Hydrocarbons | 100.0 | 100.0 | 100.0 | 100.0 | 100.0 |
| Hydrocarbon Distribution | | | | | |
| Olefins | | | | | |
| $C_2$ | 0.2 | 0.4 | 1.4 | 4.7 | 10.0 |
| $C_3$ | 1.3 | 3.2 | 6.1 | 11.6 | 17.9 |
| $1 + i\text{-}C_4$ | 0.2 | 0.6 | 1.1 | 2.1 | 3.4 |
| $2\text{-}C_4$ | 0.0 | 0.9 | 1.5 | 2.5 | 3.7 |
| Selectivity | 1.7 | 5.1 | 10.1 | 20.9 | 35.0 |
| Paraffins | | | | | |
| $C_1$ | 62.5 | 58.7 | 53.2 | 45.7 | 39.8 |
| $C_2$ | 16.1 | 16.2 | 16.3 | 13.7 | 9.4 |
| $C_3$ | 9.3 | 9.8 | 9.5 | 7.7 | 5.1 |
| $i\text{-}C_4$ | 0.9 | 0.9 | 1.2 | 1.1 | 0.7 |
| $n\text{-}C_4$ | 1.2 | 1.5 | 1.5 | 1.2 | 0.7 |
| Selectivity | 90.0 | 87.1 | 81.7 | 69.4 | 55.7 |
| $C_5 +$ - Aliphatics | 0.1 | 0.2 | 0.6 | 1.3 | 1.3 |
| Aromatics | | | | | |
| Benzene | 1.6 | 1.4 | 1.4 | 1.4 | 1.2 |
| Toluene | 4.8 | 4.3 | 4.3 | 4.3 | 4.3 |
| $C_8$ | 1.8 | 1.9 | 1.9 | 2.7 | 2.5 |
| $C_9+$ | 0.0 | 0.0 | 0.0 | 0.0 | 0.0 |
| Selectivity | 8.2 | 7.6 | 7.6 | 8.4 | 8.0 |

[a]catalyst = 400 mg, C2Cl4 = 5.3 mg/min, H2 = 30 ml/min, WHSV = 0.8 hr$^{-1}$.

Conversions of fluorine containing reactants were successfully carried out using the perhalogenated reactant trichlorotrifluoroethane, $C_2Cl_3F_3$, over a 10% Ni/ZSM-5/Al2O3 catalyst. Complete conversion of the starting material was obtained and maintained over a 4 hour period at a reaction temperature of 425° C., a $C_2Cl_3F_3$ WHSV of 0.99 hr$^{-1}$ and a [H2]/[$C_2Cl_3F_3$] ratio of 30 to 1. The hydrocarbon product distribution obtained consisted primarily of paraffins (90%) and olefins with virtually no aromatics observed.

REFERENCES

Bartholomew, C. H. and Farrauto, R. J., *J. Catlysis,* 45, 41 (1976).

Butler, S. A., Jurewicz, A. T. and Kaeding, W. W., U.S. Pat. No. 3,894,107, Jul. 8, 1975.

Chuang, S. C. and Bozzelli, J. W., *Ind. Eng. Chem. Process. Des. Dev.,* 25, 321 (1986).

Deisen, R. W., U.S. Pat. No. 4,384,159, May 17, 1983.

Gokhberg, P. Ya, No, B. I., Zaidman, O. A. and Grinberg, S. B., *Kinetica i Kataliz,* 30, 1376 (1989).

Imamura, S. and Tarumoto, H., *Ind. Eng. Chem. Res.,* 28, 1449–1452 (1989).

Oku, A. and Kimura, K., *Chemistry Express,* 5, 181-184 (1990).

Weiss, A. H. and Valinski, S., *J. Catalysis,* 74, 136 (1982).

What is claimed is:

1. A process for complete hydrodehalogenation of an aliphatic or alicyclic halogenated hydrocarbon to form a nonhalogenated hydrocarbon product, comprising contracting said aliphatic or alicyclic halogenated hydrocarbon in the gaseous phase with an elemental nickel-containing zeolite catalyst in the presence of a hydrogen donor at a temperature of about 300° C. to about 500° C.

2. The process of claim 1 wherein the aliphatic halogenated hydrocarbon comprises a brominated, fluorinated, or chlorinated compound.

3. The process of claim 1 wherein the hydrogen donor comprises hydrogen, water or methanol.

4. The process of claim 1 wherein the hydrogen donor comprises water and hydrogen.

5. The process of claim 1 wherein the hydrogen donor is hydrogen.

6. The process of claim 1 wherein the catalyst is a nickel-containing ZSM-5 zeolite catalyst.

7. The process of claim 6 wherein the catalyst contains from about 1% to about 35% nickel metal.

8. The process of claim 6 wherein the catalyst contains from about 10% to about 20% nickel metal.

9. The process of claim 1 wherein the hydrodehalogenation is initiated at a temperature between about 350° and 400° C.

10. The process of claim 9 further comprising lowering the reaction temperature to about 325° C. after initiating the hydrodehalogenation.

11. The process of claim 1 wherein the aliphatic halogenated hydrocarbon comprises at least 2 chlorine atoms.

12. The process of claim 1 wherein the halogenated hydrocarbon comprises trichloroethane, trichloroethylene, dichloroethane, dichloroethylene, dichloromethane, trichloromethane, tetrachloromethane, tetrachloroethylene or dibromoethane.

13. The process of claim 1 wherein the aliphatic halogenated hydrocarbon is a perhalogenated hydrocarbon.

14. The process of claim 13 wherein the perhalogenated hydrocarbon comprises a fluorinated hydrocarbon.

15. The process of claim 14 wherein the fluorinated hydrocarbon is trichlorotrifluoroethane.

16. The process of claim 14 wherein the temperature is about 425° C. with a 10% Ni/ZSM-5/$Al_2O_3$ catalyst at WHSV of about 0.99 $hr^{-1}$ and a hydrogen to catalyst ratio of about 30 to 1.

17. The process of claim 13 wherein the aliphatic halogenated hydrocarbon is tetrachloroethylene.

* * * * *